US008551945B2

(12) United States Patent
Dent et al.

(10) Patent No.: US 8,551,945 B2
(45) Date of Patent: Oct. 8, 2013

(54) METHODS AND COMPOSITIONS FOR TREATING NEUROPATHIES

(75) Inventors: Carolyn Dent, Richmond, CA (US); Josee Laganiere, El Cerrito, CA (US); Xiangdong Meng, San Pablo, CA (US); David Paschon, Oakland, CA (US); Siyuan Tan, Alameda, CA (US); Lei Zhang, Davis, CA (US); Steve H. Zhang, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 425 days.

(21) Appl. No.: 12/658,258

(22) Filed: Feb. 4, 2010
(Under 37 CFR 1.47)

(65) Prior Publication Data
US 2011/0082078 A1 Apr. 7, 2011

Related U.S. Application Data

(60) Provisional application No. 61/206,770, filed on Feb. 4, 2009.

(51) Int. Cl.
*A61K 38/00* (2006.01)
*A61K 38/28* (2006.01)
*A61P 3/10* (2006.01)
*A61P 7/12* (2006.01)
*A61P 25/02* (2006.01)
*C12N 5/00* (2006.01)
*C12N 5/02* (2006.01)
*C07K 1/00* (2006.01)
*C07K 14/00* (2006.01)
*C07K 16/00* (2006.01)
*C07K 17/00* (2006.01)
*C07H 21/04* (2006.01)

(52) U.S. Cl.
USPC ........... 514/6.9; 514/18.2; 435/325; 530/400; 536/23.5

(58) Field of Classification Search
USPC ................. 514/6.9, 18.2; 435/325; 530/400; 536/23.5
See application file for complete search history.

(56) References Cited

U.S. PATENT DOCUMENTS

| | | | |
|---|---|---|---|
| 5,176,996 A | 1/1993 | Hogan et al. |
| 5,422,251 A | 6/1995 | Fresco |
| 5,789,538 A | 8/1998 | Rebar et al. |
| 5,925,523 A | 7/1999 | Dove et al. |
| 5,928,638 A | 7/1999 | Uchida et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox et al. |
| 6,689,558 B2 | 2/2004 | Case |
| 6,794,136 B1 | 9/2004 | Eisenberg et al. |
| 6,824,978 B1 | 11/2004 | Cox et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox et al. |
| 7,153,949 B2 | 12/2006 | Kim et al. |
| 7,163,824 B2 | 1/2007 | Cox et al. |
| 7,253,273 B2 | 8/2007 | Collingwood |
| 7,262,054 B2 | 8/2007 | Jamieson et al. |
| 7,361,635 B2 | 4/2008 | Miller et al. |
| 2002/0115215 A1 | 8/2002 | Wolffe et al. |
| 2002/0160940 A1 | 10/2002 | Case et al. |
| 2003/0082552 A1 | 5/2003 | Wolffe et al. |
| 2005/0064474 A1 | 3/2005 | Urnov et al. |
| 2005/0245476 A1 | 11/2005 | Collingwood et al. |
| 2005/0267061 A1 | 12/2005 | Martin |
| 2006/0040880 A1 | 2/2006 | Forsayeth et al. |
| 2006/0188987 A1 | 8/2006 | Guschan et al. |
| 2007/0218528 A1 | 9/2007 | Miller et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |

(Continued)

OTHER PUBLICATIONS

Airaksinen, et al., "The GDNF Family: Signalling, Biological Functions and Therapeutic Value," *Nature Rev Neurosci* 3:384-394 (2002).
Beerli, et al., "Engineering Polydactyl Zinc-Finger Transcription Factors," *Nature Biotechnology* 20:135-141 (2002).
Choo, et al., "Advances in Zinc Finger Engineering," *Curr. Opin. Struct. Biol.* 10:411-416 (2000).
Christine, et al., "Safety and Tolerability of Putaminal AADC Gene Therapy for Parkinson Disease," *Neurology* 73:1662-1669 (2009).
de la Rosa, et al., "Role of Neurotrophins in the Control of Neural Development: Neurotrophin-3 Promotes Both Neuron Differentiation and Survival of Cultured Chick Retinal Cells," *Neuroscience* 58:347-352 (1994).
Dull, et al., "A Third-Generation Lentivirus Vector With a Conditional Packaging System," *J. Virol.* 72:8463-8471 (1998).
Eberling, et al., "Results From a Phase I Safety Trial of HAADC Gene Therapy for Parkinson Disease," *Neurology* 70:1980-1983 (2008).
Eberling, et al., "Functional Effects of AAV2-GDNF on the Dopaminergic Nigrostriatal Pathway in Parkinsonian Rhesus Monkeys," *Hum Gene Ther* 20:511-518 (2009).

(Continued)

*Primary Examiner* — Tracy Vivlemore
*Assistant Examiner* — Genevieve S Alley
(74) *Attorney, Agent, or Firm* — Pasternak Patent Law; Dahna S. Pasternak

(57) ABSTRACT

Disclosed herein are methods and compositions for treating neuropathies by modulating endogenous NT-3 of GDNF gene expression.

16 Claims, 17 Drawing Sheets

(56) References Cited

FOREIGN PATENT DOCUMENTS

| WO | WO 98/54311 A1 | 12/1998 |
| --- | --- | --- |
| WO | WO 00/27878 A1 | 5/2000 |
| WO | WO 00/41566 A1 | 7/2000 |
| WO | WO 01/60970 A2 | 8/2001 |
| WO | WO 01/88197 A2 | 11/2001 |
| WO | WO 02/16536 A1 | 2/2002 |
| WO | WO 02/44376 A2 | 6/2002 |
| WO | WO 02/077227 A2 | 10/2002 |
| WO | WO 02/099084 A2 | 12/2002 |
| WO | WO 03/016496 A2 | 2/2003 |
| WO | WO 2005/100392 A2 | 10/2005 |

OTHER PUBLICATIONS

Fiandaca, et al., "Real-Time MR Imaging of Adeno-Associated Viral Vector Delivery to the Primate Brain," *Neuroimage* 47 Suppl 2:T27-T35 (2009).

Fitzsimmons, et al., "Further Validation of the Corridor Task for Assessing Deficit and Recovery in the Hemi-Parkinsonian Rat: Restoration of Bilateral Food Retrieval by Dopamine Receptor Agonism," *Behav Brain Res* 169:352-355 (2006).

Frasson, et al., "Glial Cell Line-Derived Neurotrophic Factor Induces Histologic and Functional Protection of Rod Photoreceptors in the RD/RD Mouse," *Invest Ophthalmol Vis Sci* 40:2724-2734 (1999).

Gill, et al., "Direct Brain Infusion of Glial Cell Line-Derived Neurotrophic Factor in Parkinson Disease," *Nat Med* 9:589-595 (2003).

Green-Sadan, et al., "Glial Cell Line-Derived Neurotrophic Factor-Conjugated Nanoparticles Suppress Acquisition of Cocaine Self-Administration in Rats," *Exp Neurol* 194:97-105 (2005).

Hovland, et al., "Six-Month Continuous Intraputamenal Infusion Toxicity Study of Recombinant Methionyl Human Glial Cell Line-Derived Neurotrophic Factor (R-METHUGDNF) in Rhesus Monkey," *Toxicol Pathol* 35:1013-1029 (2007).

Idelson, et al., "Directed Differentiation of Human Embryonic Stem Cells Into Functional Retinal Pigment Epithelium Cells," *Cell Stem Cell* 5:396-408 (2009).

Isalan et al., "A Rapid, Generally Applicable Method to Engineer Zinc Fingers Illustrated by Targeting the HIV-1 Promoter," *Nat Biotechnol* 19:656-660 (2001).

Isner, et al., "VEGF Gene Transfer for Diabetic Neuropathy," *Hum Gene Ther* 10:1593-1594 (2001).

Jamieson, et al., "Drug Discovery With Engineered Zinc-Finger Proteins," *Nature Reviews Drug Discovery* 2(5):361-368 (2003).

Kells, et al., "AAV-Mediated Gene Delivery of BDNF or GDNF is Neuroprotective in a Model of Huntington Disease," *Mol Ther* 9:682-688 (2004).

Lang, et al., "Randomized Controlled Trial of Intraputamenal Glial Cell Line-Derived Neurotrophic Factor Infusion in Parkinson Disease," *Ann Neurol* 59:459-466 (2006).

Mata, et al., "Gene Therapy for the Treatment of Sensory Neuropathy," *Expert Opin Biol Ther* 6:499-507 (2006).

McGee Sanftner, et al. "Glial Cell Line Derived Neurotrophic Factor Delays Photoreceptor Degeneration in a Transgenic Rat Model of Retinitis pigmentosa," *Mol Ther* 4:622-629 (2001).

Oiwa, et al., "Progressive and Extensive Dopaminergic Degeneration Induced by Convection-Enhanced Delivery of 6-Hydroxydopamine Into the Rat Striatum: A Novel Rodent Model of Parkinson Disease," *Neurosurg* 98:136 (2003).

Pabo, et al., "Design and Selection of Novel CYS2-HIS2 Zinc Finger Proteins," *Ann. Rev. Biochem.* 70:313-340 (2001).

Pascual, et al., "Absolute Requirement of GDNF for Adult Catecholaminergic Neuron Survival," *Nat Neurosci* 11:755-761 (2008).

Peterson, et al., "Treatment of Parkinson's Disease With Trophic Factors," *Neurotherapeutics* 5:270-280 (2008).

Pradat, et al., "Continuous Delivery of Neurotrophin 3 by Gene Therapy Has a Neuroprotective Effect in Experimental Models of Diabetic and Acrylamide Neuropathies," *Hum Gene Ther* 12:2237-2249 (2001).

Sahenk, et al., "NT-3 Promotes Nerve Regeneration and Sensory Improvement in CMT1A Mouse Models and in Patients," *Neurology* 65:681-689 (2005).

Segal, et al., "Custom DNA-Binding Proteins Come of Age: Polydactyl Zinc-Finger Proteins," *Curr. Opin. Biotechnol.* 12:632-637 (2001).

Schallert, et al., "CNS Plasticity and Assessment of Forelimb Sensorimotor Outcome in Unilateral Rat Models of Stroke, Cortical Ablation, Parkinsonism and Spinal Cord Injury," *Neuropharmacology* 39:777-787 (2000).

Schratzberger, et al., "Reversal of Experimental Diabetic Neuropathy by VEGF Gene Expression," *J Clin Inv* 107:1083-1092 (2001).

Slevin, et al., "Improvement of Bilateral Motor Functions in Patients With Parkinson Disease Through the Unilateral Intraputaminal Infusion of Glial Cell Line-Derived Neurotrophic Factor," *J Neurosurg* 102:216-222 (2005).

Sondell, et al., "Vascular Endothelial Growth Factor Has Neurotrophic Activity and Stimulates Axonal Outgrowth, Enhancing Cell Survival and Schwann Cell Proliferation in the Peripheral Nervous System," *J Neurosciences* 19:5731-5740 (1999).

Sondell, et al., "Vascular Endothelial Growth Factor is a Neurotrophic Factor Which Stimulates Axonal Outgrowth Through the FLK-1 Receptor," *European J Neurosciences* 12:4243-4254 (2000).

Tiscornia, et al., "Production and Purification of Lentiviral Vectors," *Nature Protocols* 1:241-245 (2006).

Wang, et al., "Neuroprotective Effects of Glial Cell Line-Derived Neurotrophic Factor Mediated by an Adeno-Associated Virus Vector in a Transgenic Animal Model of Amyotrophic Lateral Sclerosis," *J Neurosci* 22:6920-6928 (2002).

Wilson-Gerwing, et al., "Neurotrophin-3 Significantly Reduces Sodium Channel Expression Linked to Neuropathic Pain States," *Exp Neurol* 213:303-314 (2008).

Young, et al., "Nerve Growth Factor and Neurotrophin-3 Affect Functional Recovery Following Peripheral Nerve Injury Differently," *Restor Neurol Neurosci* 18:167-175 (2001).

Zhang, et al., "An Engineered Zinc Finger Transcriptionsl Activator of the Glial Cell Line-Derived Neurotrophic Factor Provides Functional Neuroprotection in a Rat Model of Parkinson's Disease," Poster Abstract from Soc Neurosci Ann Meeting Oct. 20, 2009 available online at http://www.abstractsonline.com/Plan/View/Abstract.aspx?sKey=f3cba4c5-c866-4b06-affa-4add7dbldb82&cKey=2e029fd2-6f81-4e34-9ac7-e40b9bc9735d&mKey={081F7976-E4CD-4F3D-A0AF-E8387992A658}.

Zufferey, et al., "Self-Inactivating Lentivirus Vector for Safe and Efficient In Vivo Gene Delivery," *J. Virol.* 72:9873-9880 (1998).

A.

| NLS | ZFP | p65 | Flag |
|-----|-----|-----|------|

B. 11971 ZFP – Six zinc finger modules

| Finger | 6F | 5F | 4F | 3F | 2F | 1F |
|--------|----|----|----|----|----|----|
| Target Triplet | 5'-GGA | GCC | ATC | TGG | CCG | GGT |
| Design | QSGHLSR SEQ ID NO:3 | DRSDLSR SEQ ID NO:4 | DSSARKK SEQ ID NO:5 | RSDHLST SEQ ID NO:6 | RSDDRKT SEQ ID NO:7 | QSSHLTR SEQ ID NO:8 |

C. 17248 ZFP - six finger modules

| Finger | N-6F | 5F | 4F | 3F | 2F | 1F-C |
|--------|------|----|----|----|----|------|
| Target Triplet | 5' ACA | TGG | CAG | GCA | ATG | AAG-3' |
| Recognition Helix | QNATRIN SEQ ID NO:37 | RSDHLST SEQ ID NO:6 | RSDNLRE SEQ ID NO:36 | QSGSLTR SEQ ID NO:35 | RNASRIT SEQ ID NO:34 | RSDNLSV SEQ ID NO:33 |

FIGURE 1

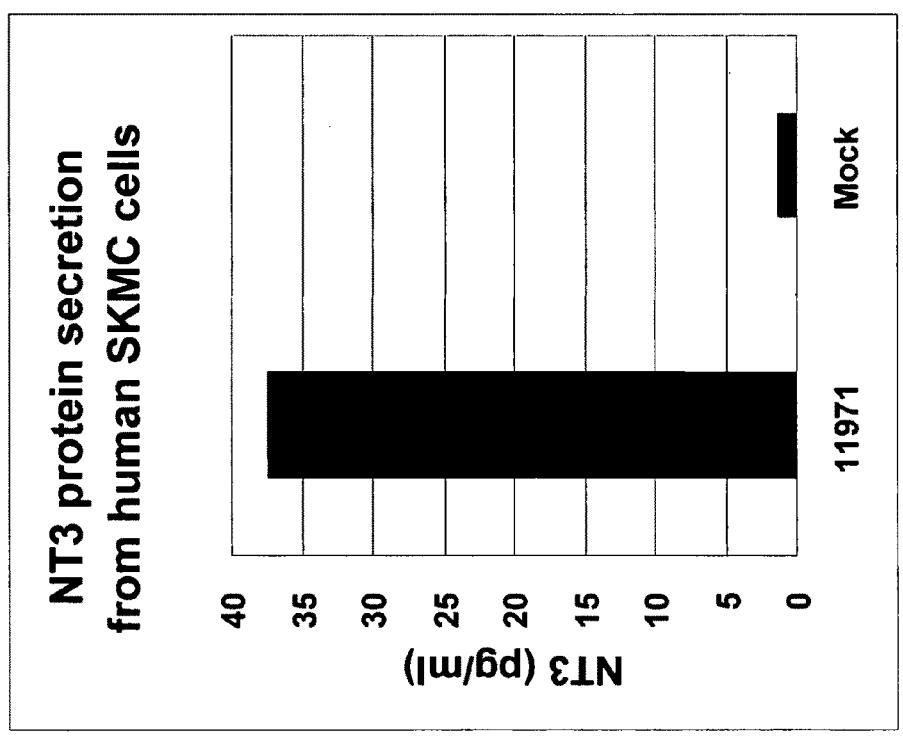

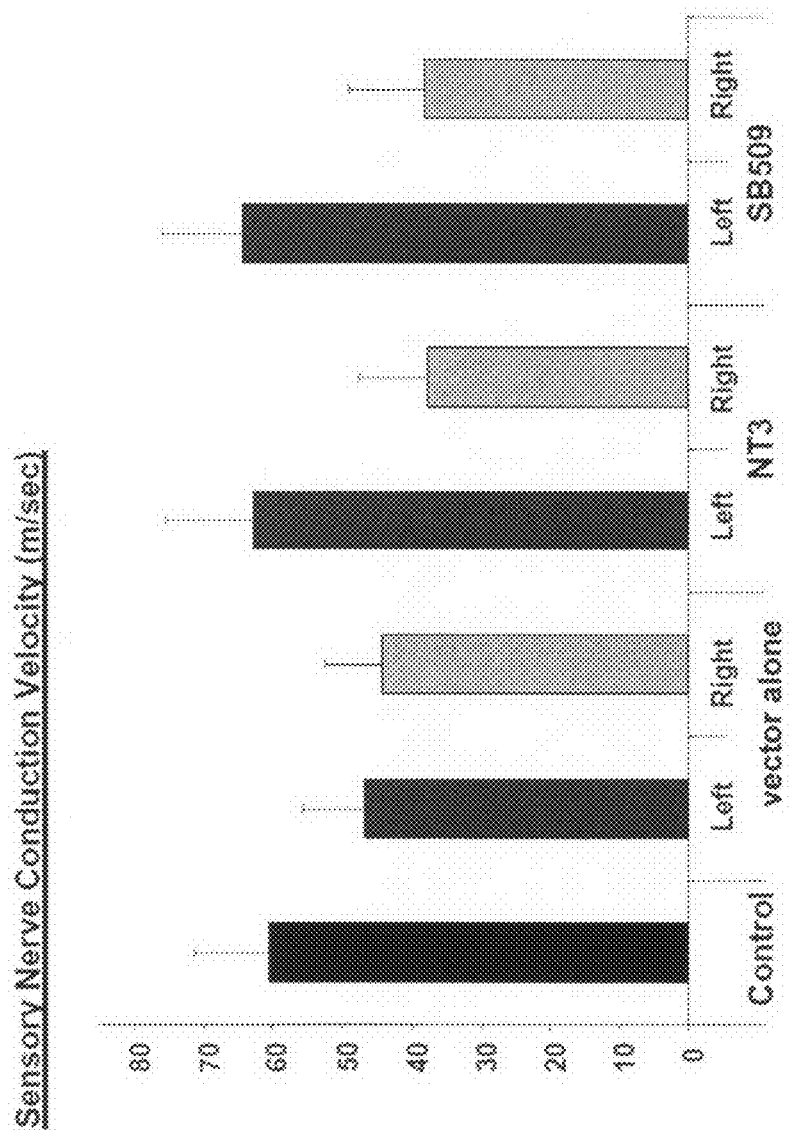

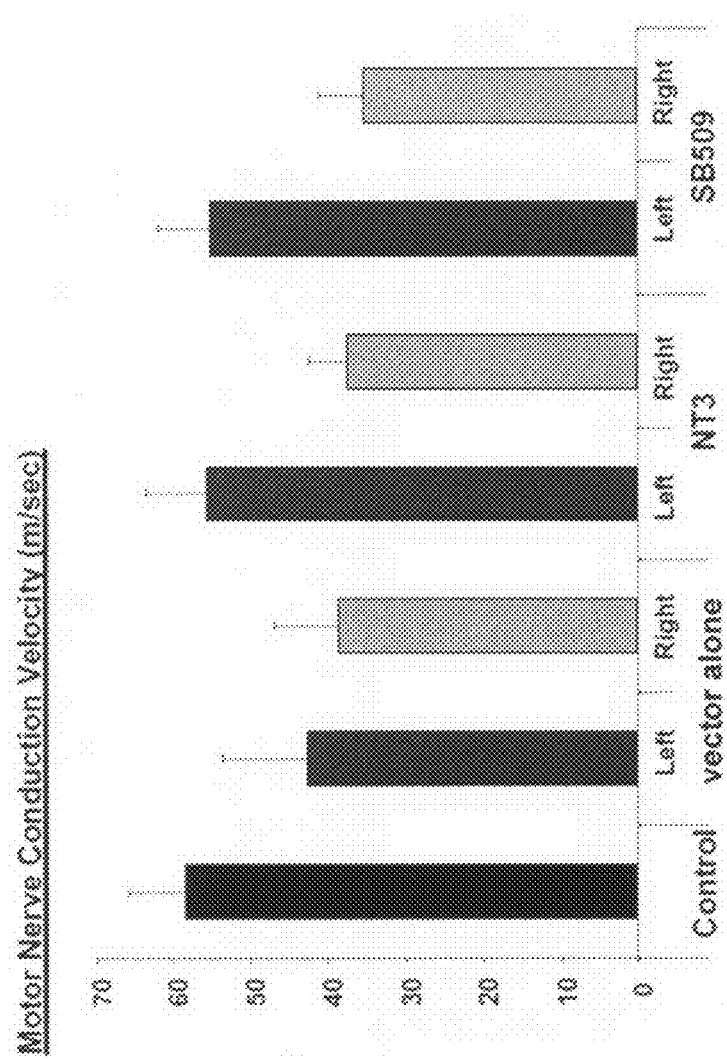

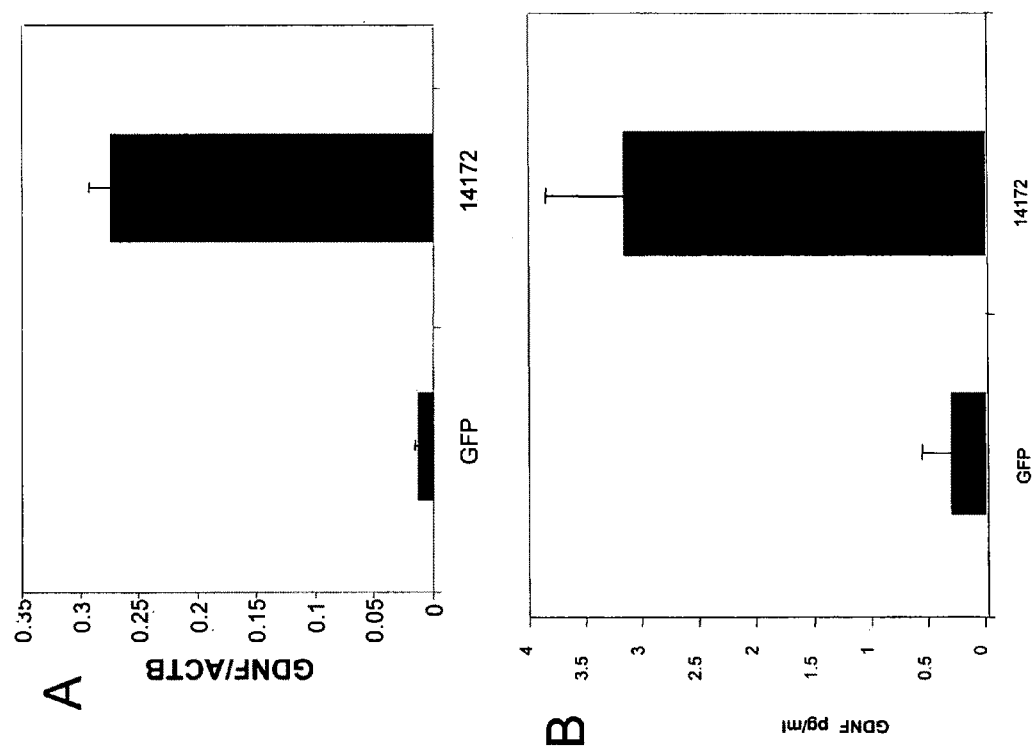

SEQUENCE LISTING

```
<160> NUMBER OF SEQ ID NOS: 92

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide: nuclear localization signal
      (NLS) from SV40 large T antigen

<400> SEQUENCE: 1

Pro Lys Lys Lys Arg Lys Val
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide: flag epitope tag (Flag)

<400> SEQUENCE: 2

Asp Tyr Lys Asp Asp Asp Asp Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 3

Gln Ser Gly His Leu Ser Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 4

Asp Arg Ser Asp Leu Ser Arg
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 5

Asp Ser Ser Ala Arg Lys Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide: NT-3 and GDNF targeted zinc
      finger protein

<400> SEQUENCE: 6

Arg Ser Asp His Leu Ser Thr
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide: NT-3 and GDNF targeted zinc
      finger protein

<400> SEQUENCE: 7

Arg Ser Asp Asp Arg Lys Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 8

Gln Ser Ser His Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 9

Arg Pro Asp Asp Arg Asn Gln
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein
```

```
<400> SEQUENCE: 10

Arg Lys Asp Cys Arg Thr Gln
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 11

Arg His Asp Val Leu Ala Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 12

Arg Gln Asp Val Arg Leu Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 13

Gln Pro Ser Met Leu Arg Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 14

Thr Ala His Glu Arg Thr Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 15

Arg Arg Pro Asp Leu Thr Arg
1               5

<210> SEQ ID NO 16
<211> LENGTH: 7
<212> TYPE: PRT
```

```
<213> ORGANISM: Artificial Sequence
<220> FEATURE:
<223> OTHER INFORMATION: Synthetic peptide: NT-3 targeted zinc finger
      protein

<400> SEQUENCE: 16

Asp Gly Asn Thr Arg Arg Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 17

Asp Val Ser Gly Arg Arg Ala
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 18

Asp Pro Asn Thr Leu Arg Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 19

Trp Pro Gln Ser Arg Gln Arg
1               5

<210> SEQ ID NO 20
<211> LENGTH: 18
<212> TYPE: DNA
<213> ORGANISM: Unknown
<220> FEATURE:
<223> OTHER INFORMATION: Target site for NT-3 proteins from Homo sapiens
      or Rattus norvegicus

<400> SEQUENCE: 20
ggagccatct ggccgggt                                                 18

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 21

Gln Ser Gly His Leu Ala Arg
1               5
```

```
<210> SEQ ID NO 22
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 22

Asp Asn Pro Asn Leu Asn Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 23

Arg Ser Asp Asp Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 24

Asp Arg Ser His Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 25

Arg Ser Asp His Leu Ser Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 26

Arg Tyr Pro Asn Leu Ile Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 27
```

```
Gln Ser Gly Asn Leu Ala Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 28

Thr Ser Gly Asn Leu Thr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 29

Arg Ser Asp His Leu Ser Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 30

Gln Asn His His Arg Ile Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 31

Arg Ser Ala Asp Leu Thr Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 32

Gln Ser Ser Asp Leu Arg Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
```

```
                       protein

<400> SEQUENCE: 33

Arg Ser Asp Asn Leu Ser Val
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 34

Arg Asn Ala Ser Arg Ile Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 35

Gln Ser Gly Ser Leu Thr Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 36

Arg Ser Asp Asn Leu Arg Glu
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 37

Gln Asn Ala Thr Arg Ile Asn
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 38

Arg Ser Asp His Leu Ser Gln
1               5

<210> SEQ ID NO 39
<211> LENGTH: 7
```

```
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 39

Arg Ser Ala Val Arg Lys Asn
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 40

Asp Arg Ser His Leu Ala Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 41

Asp Arg Ser Ala Arg Thr Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 42

Asp Arg Asn Gln Leu Ile Asn
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 43

Arg Ser Ala Asp Leu Ser Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 44

Gln Ser Ser Asp Leu Ser Arg
1               5
```

```
<210> SEQ ID NO 45
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 45

Asp Arg Ser Asn Leu Thr Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 46

Arg Ser Asp His Leu Ser Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 47

Arg Ser Ala Asn Leu Ser Val
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 48

Tyr Gln Gly Val Leu Thr Arg
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 49

Thr Lys Arg Ala Leu Asn Gln
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein
```

```
<400> SEQUENCE: 50

Gln Gln Ser Ala Arg Thr Leu
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 51

His Arg Ser Thr Leu Leu Met
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 52

Arg Ala Asp Asn Leu Ser Val
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 53

Thr Thr Lys Gly Arg Thr His
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide: GDNF targeted zinc finger
      protein

<400> SEQUENCE: 54

Arg Arg Ser Ser Leu Arg Ser
1               5

<210> SEQ ID NO 55
<211> LENGTH: 18
<212> TYPE: DNA
<213> ORGANISM: Rat

<400> SEQUENCE: 55
gggggcgcgg aaccggga                                                 18

<210> SEQ ID NO 56
<211> LENGTH: 18
<212> TYPE: DNA
<213> ORGANISM: Unknown
<220> FEATURE:
<223> OTHER INFORMATION: Derived from human or rhesus macaque

<400> SEQUENCE: 56
```

```
gctgcgagtg gggatgaa                                                    18
```

<210> SEQ ID NO 57

<400> SEQUENCE: 57

000

<210> SEQ ID NO 58
<211> LENGTH: 18
<212> TYPE: DNA
<213> ORGANISM: Unknown
<220> FEATURE:
<223> OTHER INFORMATION: Derived from human or rhesus macaque

<400> SEQUENCE: 58

```
acatggcagg caatgaag                                                    18
```

<210> SEQ ID NO 59
<211> LENGTH: 19
<212> TYPE: DNA
<213> ORGANISM: Unknown
<220> FEATURE:
<223> OTHER INFORMATION: Derived from human or rhesus macaque

<400> SEQUENCE: 59

```
gcggagcggc cgggtgagg                                                   19
```

<210> SEQ ID NO 60
<211> LENGTH: 19
<212> TYPE: DNA
<213> ORGANISM: Unknown
<220> FEATURE:
<223> OTHER INFORMATION: Derived from human or rhesus macaque

<400> SEQUENCE: 60

```
gccaggggac gctgcgagt                                                   19
```

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide: primer

<400> SEQUENCE: 61

```
ccaacgaaga caagatctgc                                                  20
```

<210> SEQ ID NO 62
<211> LENGTH: 18
<212> TYPE: DNA
<213> ORGANISM: Artificial Sequence
<220> FEATURE:
<223> OTHER INFORMATION: Synthetic oligonucleotide: primer

<400> SEQUENCE: 62

```
tcctgcgtcg agagagct                                                    18
```

<210> SEQ ID NO 63
<211> LENGTH: 23
<212> TYPE: DNA
<213> ORGANISM: Artificial Sequence
<220> FEATURE:
<223> OTHER INFORMATION: Synthetic oligonucleotide: primer

<400> SEQUENCE: 63

```
cgcccgaaca gggacctgaa agc                                          23

<210> SEQ ID NO 64
<211> LENGTH: 25
<212> TYPE: DNA
<213> ORGANISM: Artificial Sequence
<220> FEATURE:
<223> OTHER INFORMATION: Synthetic oligonucleotide: primer

<400> SEQUENCE: 64
tgaaacatac gttcccaaag agttt                                        25

<210> SEQ ID NO 65
<211> LENGTH: 26
<212> TYPE: DNA
<213> ORGANISM: Artificial Sequence
<220> FEATURE:
<223> OTHER INFORMATION: Synthetic oligonucleotide: primer

<400> SEQUENCE: 65
ctctccttct cagaaagtgt gcatat                                       26

<210> SEQ ID NO 66
<211> LENGTH: 27
<212> TYPE: DNA
<213> ORGANISM: Artificial Sequence
<220> FEATURE:
<223> OTHER INFORMATION: Synthetic oligonucleotide: primer

<400> SEQUENCE: 66
tgctgaaaca ttcaccttcc atgcaga                                      27

<210> SEQ ID NO 67
<211> LENGTH: 26
<212> TYPE: DNA
<213> ORGANISM: Artificial Sequence
<220> FEATURE:
<223> OTHER INFORMATION: Synthetic oligonucleotide: hNT3-743F

<400> SEQUENCE: 67
gataaacact ggaactctca gtgcaa                                       26

<210> SEQ ID NO 68
<211> LENGTH: 21
<212> TYPE: DNA
<213> ORGANISM: Artificial Sequence
<220> FEATURE:
<223> OTHER INFORMATION: Synthetic oligonucleotide: hNT3-827R

<400> SEQUENCE: 68
gccagcccac gagtttattg t                                            21

<210> SEQ ID NO 69
<211> LENGTH: 29
<212> TYPE: DNA
<213> ORGANISM: Artificial Sequence
<220> FEATURE:
<223> OTHER INFORMATION: Synthetic oligonucleotide: hNT3-776P

<400> SEQUENCE: 69
caaacctacg tccgagcact gacttcaga                                    29

<210> SEQ ID NO 70
<211> LENGTH: 26
<212> TYPE: DNA
<213> ORGANISM: Artificial Sequence
<220> FEATURE:
```

```
<223> OTHER INFORMATION: Synthetic oligonucleotide: hNT3-1AF

<400> SEQUENCE: 70
agccaggata atgatgagat cttaca                                          26

<210> SEQ ID NO 71
<211> LENGTH: 28
<212> TYPE: DNA
<213> ORGANISM: Artificial Sequence
<220> FEATURE:
<223> OTHER INFORMATION: Synthetic oligonucleotide: hNT3-1AR

<400> SEQUENCE: 71
ggagataagc gagaaatatc acataaaa                                        28

<210> SEQ ID NO 72
<211> LENGTH: 18
<212> TYPE: DNA
<213> ORGANISM: Artificial Sequence
<220> FEATURE:
<223> OTHER INFORMATION: Synthetic oligonucleotide: hNT3-1APro

<400> SEQUENCE: 72
tgaacaaggt gatgtcca                                                   18

<210> SEQ ID NO 73
<211> LENGTH: 18
<212> TYPE: DNA
<213> ORGANISM: Artificial Sequence
<220> FEATURE:
<223> OTHER INFORMATION: Synthetic oligonucleotide: hNT3-1BF

<400> SEQUENCE: 73
tcgacgtccc tggaaacg                                                   18

<210> SEQ ID NO 74
<211> LENGTH: 26
<212> TYPE: DNA
<213> ORGANISM: Artificial Sequence
<220> FEATURE:
<223> OTHER INFORMATION: Synthetic oligonucleotide: hNT3-1BR

<400> SEQUENCE: 74
acataaaaca agatggacat cacctt                                          26

<210> SEQ ID NO 75
<211> LENGTH: 30
<212> TYPE: DNA
<213> ORGANISM: Artificial Sequence
<220> FEATURE:
<223> OTHER INFORMATION: Synthetic oligonucleotide: hNT3-1BPro

<400> SEQUENCE: 75
tgccatggtt acttttgcca cgatcttaca                                      30

<210> SEQ ID NO 76
<211> LENGTH: 21
<212> TYPE: DNA
<213> ORGANISM: Artificial Sequence
<220> FEATURE:
<223> OTHER INFORMATION: Synthetic oligonucleotide: hGAPDH-For

<400> SEQUENCE: 76
ccatgttcgt catgggtgtg a                                               21

<210> SEQ ID NO 77
```

```
<211> LENGTH: 20
<212> TYPE: DNA
<213> ORGANISM: Artificial Sequence
<220> FEATURE:
<223> OTHER INFORMATION: Synthetic oligonucleotide: hGAPDH-Rev

<400> SEQUENCE: 77
catggactgt ggtcatgagt                                             20

<210> SEQ ID NO 78
<211> LENGTH: 24
<212> TYPE: DNA
<213> ORGANISM: Artificial Sequence
<220> FEATURE:
<223> OTHER INFORMATION: Synthetic oligonucleotide: hGAPDH-Pro

<400> SEQUENCE: 78
tcctgcacca ccaactgctt agca                                        24

<210> SEQ ID NO 79
<211> LENGTH: 21
<212> TYPE: DNA
<213> ORGANISM: Artificial Sequence
<220> FEATURE:
<223> OTHER INFORMATION: Synthetic oligonucleotide: rNT3 778F

<400> SEQUENCE: 79
tgtgacagtg agagcctgtg g                                           21

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide: rNT3 846R

<400> SEQUENCE: 80
tgtaacctgg tgtccccgaa                                             20

<210> SEQ ID NO 81
<211> LENGTH: 26
<212> TYPE: DNA
<213> ORGANISM: Artificial Sequence
<220> FEATURE:
<223> OTHER INFORMATION: Synthetic oligonucleotide: rNT3 800P

<400> SEQUENCE: 81
tgaccgacaa gtcctcagcc attgac                                      26

<210> SEQ ID NO 82
<211> LENGTH: 21
<212> TYPE: DNA
<213> ORGANISM: Artificial Sequence
<220> FEATURE:
<223> OTHER INFORMATION: Synthetic oligonucleotide: rGAPDH-For

<400> SEQUENCE: 82
cccatgtttg tgatgggtgt g                                           21

<210> SEQ ID NO 83
<211> LENGTH: 24
<212> TYPE: DNA
<213> ORGANISM: Artificial Sequence
<220> FEATURE:
<223> OTHER INFORMATION: Synthetic oligonucleotide: rGAPDH-Rev

<400> SEQUENCE: 83
```

```
atcctgcacc accaactgct tagc                                          24
```

<210> SEQ ID NO 84
<211> LENGTH: 24
<212> TYPE: DNA
<213> ORGANISM: Artificial Sequence
<220> FEATURE:
<223> OTHER INFORMATION: Synthetic oligonucleotide: rGAPDH-Pro

<400> SEQUENCE: 84

```
atcctgcacc accaactgct tagc                                          24
```

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 85

```
Arg Ser Ser His Leu Ser Thr
1               5
```

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide: NT-3 targeted zinc finger
      protein

<400> SEQUENCE: 86

```
Arg Ser Asp His Leu Ser Ser
1               5
```

<210> SEQ ID NO 87
<211> LENGTH: 23
<212> TYPE: DNA
<213> ORGANISM: Artificial Sequence
<220> FEATURE:
<223> OTHER INFORMATION: Synthetic oligonucleotide: h-rh-GDNF RT-Forward

<400> SEQUENCE: 87

```
caaatggcag tgcttcctag aag                                           23
```

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide: h-rh-GDNF RT-Reverse

<400> SEQUENCE: 88

```
agttaagaca caaccccggt ttt                                           23
```

<210> SEQ ID NO 89
<211> LENGTH: 25
<212> TYPE: DNA
<213> ORGANISM: Artificial Sequence
<220> FEATURE:
<223> OTHER INFORMATION: Synthetic oligonucleotide: h-rh-GDNF RT-Probe

<400> SEQUENCE: 89

```
tgcagctgcc aacccagaga attcc                                         25
```

<210> SEQ ID NO 90

-continued

```
<211> LENGTH: 22
<212> TYPE: DNA
<213> ORGANISM: Artificial Sequence
<220> FEATURE:
<223> OTHER INFORMATION: Synthetic oligonucleotide: 18s RT- Forward

<400> SEQUENCE: 90
ttccgataac gaacgagact ct                                              22

<210> SEQ ID NO 91
<211> LENGTH: 19
<212> TYPE: DNA
<213> ORGANISM: Artificial Sequence
<220> FEATURE:
<223> OTHER INFORMATION: Synthetic oligonucleotide: 18s RT-Reverse

<400> SEQUENCE: 91
tggctgaacg ccacttgtc                                                  19

<210> SEQ ID NO 92
<211> LENGTH: 23
<212> TYPE: DNA
<213> ORGANISM: Artificial Sequence
<220> FEATURE:
<223> OTHER INFORMATION: Synthetic oligonucleotide: 18s RT-Probe

<400> SEQUENCE: 92
taactagtta cgcgaccccc gag                                             23
```

METHODS AND COMPOSITIONS FOR TREATING NEUROPATHIES

CROSS-REFERENCE TO RELATED APPLICATIONS

The present application claims the benefit of U.S. Provisional Application No. 61/206,770, filed Feb. 4, 2009, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of gene expression.

BACKGROUND

Many diseases and conditions result from neuropathy, including, for example, amyotrophic lateral sclerosis (ALS, also known as Lou Gehrig's disease), Parkinson's disease, retinal degeneration, Charcot-Marie-Tooth (CMT) disease, neuropathic pain and chemotherapy-induced neuropathies. Moreover, neuropathy (e.g., neuropathic pain) can result from trauma to neural tissue, such as nerve crush and spinal cord injuries. Therapies that stimulate neural regeneration would be advantageous for the treatment of these conditions.

For example, diabetic neuropathies are a family of nerve disorders caused by diabetes. People with diabetes can, over time, experience damage to nerves throughout the body. Neuropathies lead to numbness and sometimes pain and weakness in the hands, arms, feet, and legs. These neurological problems may also occur in every organ system, including the digestive tract, heart, and sex organs. People with diabetes can develop nerve problems at any time, but the longer a person has diabetes, the greater the risk. In Parkinson's Disease (PD), patients experience a loss of dopamine-secreting neurons in the substantia nigra. PD patients suffer from tremors, limb rigidity, akinesia and bradykinesia as well as a failure of postural reflexes which can lead to instability and falls. Diseases associated with retinal degeneration include diabetic retinopathy, retinitis pigmentosa and age-related macular degeneration (AMD). These diseases can lead to vision loss, and AMD is the leading cause of adult legal-blindness in the United States.

The treatment options for neural degenerative conditions are currently limited. For example, diabetic neuropathies are currently treated primarily by controlling the diabetic condition per se. U.S. Patent Publication No. 20050267061 describes a treatment of neuropathies using zinc finger transcription factors that modulate VEGF-A expression. U.S. Pat. No. 7,253,273 disclose zinc finger proteins targeted to Nav1.8, TrkA and VR1 for treatment of neuropathic pain. Treatment for PD is tied to symptom management. The most widely used form of treatment is L-Dopa, but over time, use of exogenous L-Dopa causes a decrease in endogenous L-Dopa production, and eventually becomes counter productive.

Several groups have also reported that administration of neurotrophic molecules per se may help ameliorate nerve degeneration. For example, Schratzberger et al. (2001) *J. Clin. Inv.* 107, 1083-1092, demonstrated that gene transfer of vascular endothelial growth factor (VEGF) could reverse diabetic neuropathy characterized by a loss of axons and demyelination in the rat experimental model. In addition, see, Isner et al. (2001) *Hum Gene Ther.* 10; 12(12):1593-4; Sondell et al. (2000) *European J. Neurosciences* 12:4243-4254; Sondell (1999) *J. Neurosciences* 19(14):5731-5740.

The neurotropic factor, NT-3, has been shown to function in promoting the survival, growth and differentiation of neurons, whereas NT-3 deficiency results in an impairment in the peripheral nervous system. NT-3 deficiency is also linked to neuropathy in experimental diabetic rats. Although gene transfer of NT-3 cDNA has shown preclinical efficacy against neuropathy in a various neuropathy animal models, the NT-3 based therapy has not been used in the clinic because of the potential problems associated with the use of NT-3 cDNA or recombinant NT-3 proteins. The direct use of NT-3 recombinant protein is limited by its short half-life, poor bioavailability and dose-limiting toxicities. See, Pradat et al. (2001) *Hum. Gene Ther.* 12:2237-2249; Young et al. (2001) *Restor Neurol. Neurosci.* 18:167-175; Mata et al. (2006) *Expert Opin Biol. Ther.* 6:499-507. In addition, gene transfer of NT-3 cDNA may lead to the over-production of NT-3 protein, resulting in unwanted toxicities.

Another neurotrophic factor that has been shown to be a potent survival factor for many different types of neuronal cells, such as dopaminergic neurons, striatal neurons, motor neurons and photoreceptor cells is glial cell line-derived neurotrophic factor (GDNF). See, e.g., Airaksinen et al. (2002) *Nature Rev Neurosci.* 3:384-394. However, no overall symptomatic improvement was observed in Phase 2 studies of Parkinson's patients receiving infusions of recombinant glial cell line-derived neurotrophic factor (GDNF). See, e.g., Lang (2006) *Ann Neurol* 59:459-466. Furthermore, Lang et al. reported that recombinant GDNF infusion resulted in significant side effects (e.g. generation of neutralizing antibodies reactive against both recombinant and endogenous GDNF), likely caused by imprecise delivery of the high doses of the recombinant protein.

Thus, there remains a need for compositions and methods for the treatment of neuropathies such as diabetic neuropathy, neuropathic pain, and various neurodegenerative conditions characterized by the loss or death of neurons or the failure of damaged neurons to regenerate.

SUMMARY

Disclosed herein are methods and compositions for treating neuropathies such as neurodegenerative diseases (e.g., Parkinson's), diabetic neuropathy and neuropathic pain. In particular, methods and compositions for modulating endogenous neurotropic factors such as NT-3 and GDNF so as to treat neuropathies are described.

Thus, in one aspect, engineered zinc finger proteins that modulate expression of NT-3 or GDNF are provided. Engineered zinc finger proteins are non-naturally occurring zinc finger proteins whose recognition helices have been altered (e.g., by selection and/or rational design) to bind to a preselected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). In certain embodiments, the zinc finger proteins have one or more of the recognition helices shown in Tables 1 or 2.

In certain embodiments, the zinc finger proteins (ZFPs) as described herein can be placed in operative linkage with a regulatory domain (or functional domain) as part of a fusion protein. By selecting either an activation domain or repression domain for fusion with the ZFP, such fusion proteins can be used either to activate or to repress gene expression. For example, a fusion protein comprising an NT-3- or GDNF-targeted ZFP as described herein and a transcriptional activation domain (e.g., VP16) can be used to upregulate endogenous NT-3 or GDNF expression, respectively.

In yet another aspect, a polynucleotide encoding any of the zinc finger proteins described herein is provided.

Additionally, pharmaceutical compositions containing the nucleic acids and/or ZFPs (or fusion proteins comprising the ZFPs) are also provided. For example, certain compositions include a nucleic acid comprising a sequence that encodes one of the ZFPs described herein operably linked to a regulatory sequence, combined with a pharmaceutically acceptable carrier or diluent, wherein the regulatory sequence allows for expression of the nucleic acid in a cell. Protein based compositions include a ZFP as disclosed herein and a pharmaceutically acceptable carrier or diluent.

In yet another aspect also provided is an isolated cell comprising any of the proteins, polynucleotides and/or compositions as described herein. In some embodiments, the cell is a stem cell.

In another aspect, provided herein are methods for treating and/or preventing neural degeneration, as well as methods for stimulating neural regeneration, using the compositions disclosed herein. In certain embodiments, the methods involve treatment of a diabetic neuropathy. In other embodiments, the methods involve treatment of Parkinson's disease. In other embodiments, the methods involve the treatment of retinal degeneration. The polynucleotides and/or proteins may be delivered using a viral vector, a non-viral vector (e.g., plasmid) and/or combinations thereof. In some embodiments, the polynucleotides and/or proteins are in a stem cell that is administered to a subject in need thereof.

In yet another aspect, provided herein are methods for treating or preventing addictive behaviors. In certain embodiments, the methods involve the treatment of alcohol addiction, and in other embodiments, the methods involve treatment of drug addiction.

These and other aspects will be readily apparent to the skilled artisan in light of disclosure as a whole.

BRIEF DESCRIPTION OF THE DRAWINGS

FIG. 1, panels A and B, depict an exemplary zinc finger protein fusion constructs as described herein. FIG. 1A is a schematic depicting a fusion protein comprising an NT-3 or GDNF ZFP and the p65 transcriptional activation domain from NF-kB. The fusion protein also comprises a nuclear localization signal (NLS) from SV40 large T antigen comprising the amino acid sequence PKKKRKV (SEQ ID NO:1) and the flag epitope tag (Flag) comprising the amino acid sequence DYKDDDDK (SEQ ID NO:2). FIG. 1B shows the NT-3 ZFP-TF designated 11971, including the recognition helices of each of the 6 fingers (1F to 6F) of 11971 as well as the target nucleotide triplet recognized by each finger. FIG. 1C shows a GDNF ZFP-TF designated 17248. Finger designs indicate the identity of amino acid residues at positions "−1" to "+6" of the alpha helix of each finger.

FIG. 2, panels A and B, are graphs depicting NT-3 expression in human primary skeletal muscle (SKMC) cells using NT-3 targeted ZFP-TFs. FIG. 2B shows an increase in NT-3 protein secretion from human SKMC cells transduced with a lentiviral vector encoding ZFP-TF 11971-p65 (shown on graph as "11971") as compared to cells transduced in the absence of a lentiviral vector ("mock").

FIG. 3A shows the activation of NT-3 mRNA, normalized to rat GAPDH mRNA, in rat SKMC cells transduced with a lentiviral vector encoding ZFP-TF 11971-p65 at a multiplicity of infection of 10~50. FIG. 3B shows an increase in NT-3 protein secretion from rat SKMC cells transduced with a lentiviral vector encoding ZFP-TF 11971-p65. 11971 refers to 11971-p65 as compared to Green Fluorescent Protein ("GFP") control non-transduced cells ("mock").

FIG. 4, panels A and B, are graphs depicting nerve conduction velocity (in m/sec) in three experimental groups of diabetic rats receiving the following plasmid injections: the "vector alone" group received the pVAX-1 vector as a sham treatment, the "NT3" group received the pVAX vector encoding the NT-3 targeted ZFP 11971 and the "SB509" group received the pVAX vector encoding the VEGF-A activating zinc finger transcription factor SB509. Age- and weight-matched rats were used as non-diabetic controls. The bar charts show sensory nerve conduction velocities (SNCVs) (A) and motor nerve conduction velocities (MNCVs) (B) data as group means+/−standard deviation for injected (left) and uninjected (right) limbs FIG. 4A shows sensory nerve conduction velocity. FIG. 4B shows motor nerve conduction velocity.

FIG. 5, panels A and B, are graphs depicting activation of GDNF in rat primary striatal neurons. FIG. 5A shows the activation of GDNF mRNA (rGDNF), normalized to rat beta actin mRNA. Rat striatal neurons cells were transduced with a lentiviral vector encoding ZFP-TF 14172-p65 or a Green Fluorescent Protein (GFP) control at a multiplicity of infection of ~10. FIG. 5B shows an increase in GDNF protein secretion in the supernatant of rat striatal neurons transduced with a lentiviral vector encoding ZFP-TF 14172-p65 or GFP at a multiplicity of infection of ~10. Lentiviral vector encoding GFP was used as a control.

FIG. 8A shows results one week post 6-OHDA lesion and FIG. 8B shows results two weeks post 6-OHDA lesion.

FIG. 11A shows results in rats receiving AAV vectors carrying GDNF-ZFP-TF 14172. FIG. 11B shows results in 6-OHDA-treated rats infused with a control AAV vector or an AAV vector carrying GDNF-ZFP-TF 16655.

FIG. 15A shows stimulation of GDNF expression in normal rats injected suboccularly with the ZFP-TF-14172 construct. FIG. 15B shows preservation of cone function in RCS rats injected with the ZFP-TF-16655 construct.

DETAILED DESCRIPTION

Figure 2A:
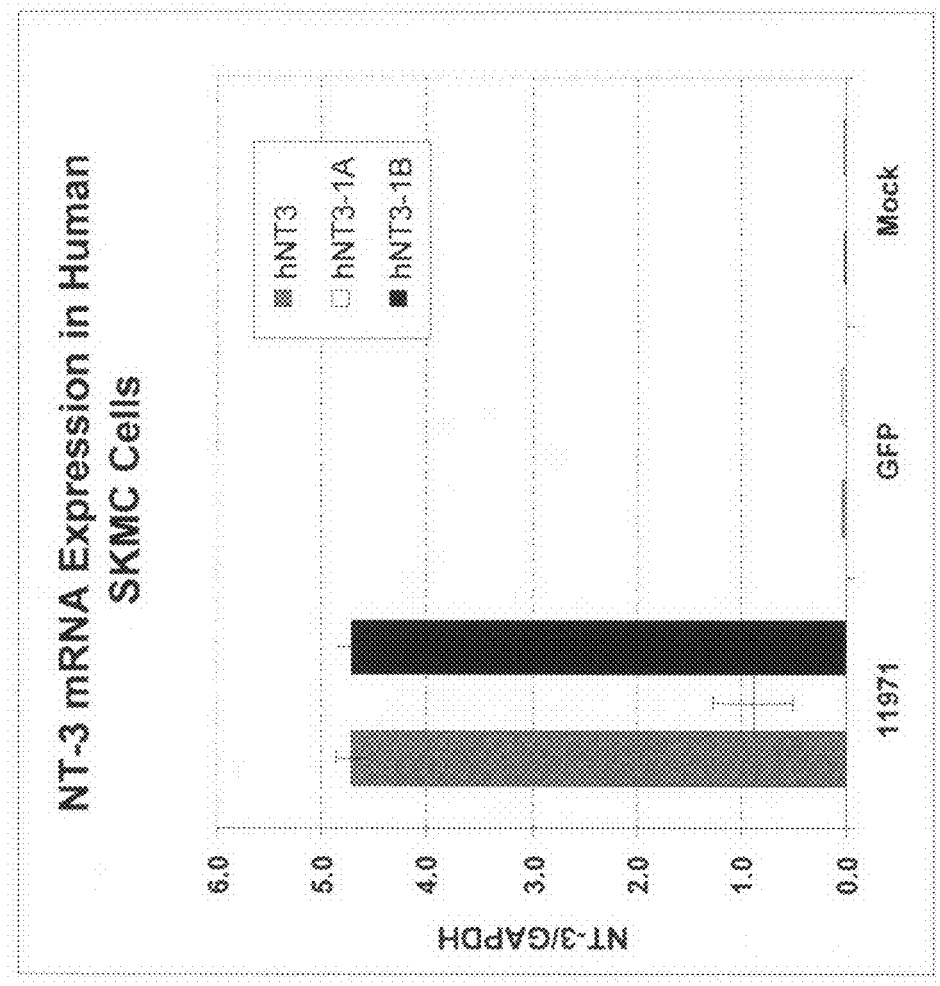
FIG. 2A shows the activation of NT-3 total mRNA (hNT3, light gray), as well as its alternative transcripts 1A (hNT3-1A, white) and 1B (hNT3-1B, dark grey), normalized to human glyceraldehyde-3-phosphate dehydrogenase (GAPDH) mRNA, in human SKMC cells transduced with a lentiviral vector encoding ZFP-TF 11971-p65 at a multiplicity of infection of 10~50.

Disclosed herein are compositions and methods for treating neuropathic conditions such as diabetic neuropathy, Parkinson's disease, Charcot-Marie-Tooth disease, retinal degeneration, addictive behaviors, chemotherapy-induced neuropathy and the like. In particular, NT-3 and GDNF modulating transcription factors comprising zinc finger proteins (ZFPs) and methods utilizing such proteins are provided for use in treating neuropathies. These include engineered zinc finger proteins, i.e., non-naturally occurring proteins which bind to a predetermined nucleic acid target sequence.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Therefore, engineered zinc finger proteins are proteins that are non-naturally occurring. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. Exemplary target sites for various NT-3 targeted ZFPs are shown in Tables 2 and 3.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequenced may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to upregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

The term "neuropathy" includes any pathology or abnormality of neural tissue, including but not limited to, degeneration of central and peripheral nervous system tissue. Central and peripheral nervous system tissue includes, but is not limited to, any part of any neuron, including specialized neurons such as rods and cones in the eye. Thus, non-limiting examples of conditions characterized by neuropathy include amyotrophic lateral sclerosis (ALS, also known as Lou Gehrig's disease), Parkinson's disease, Alzheimer's, diabetic neuropathy, retinal degeneration, Charcot-Marie-Tooth (CMT) disease, neuropathic pain, chemotherapy-induced neuropathies, trauma (brain or spinal cord) and the like. The term also includes addictive behaviors such as alcohol or drug addiction. Other neuropathic (neurodegenerative) conditions will be known to the skilled artisan.

DNA-Binding Domains

Described herein are compositions comprising a DNA-binding domain that specifically bind to a target site in an NT-3 gene or in a GDNF gene. Any DNA-binding domain can be used in the compositions and methods disclosed herein.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263: 163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

In some embodiments, the DNA binding domain is an engineered domain from a TAL effector derived from the plant pathogen Xanthomonas (see Boch et al, (2009) *Science* 29 Oct. 2009 (10.1126/science.117881) and Moscou and Bogdanove, (2009) *Science* 29 Oct. 2009 (10.1126/science.1178817).

In one embodiment, the DNA binding domain is an engineered zinc finger protein that binds (in a sequence-specific manner) to a target site in an NT-3 gene and modulates expression of NT-3. In another embodiment, the DNA binding domain is an engineered zinc finger protein that binds (in a sequence-specific manner) to a target site in a GDNF gene and modulates expression of GDNF. The ZFPs that bind to selected NT-3 or GDNF target sites typically include at least one zinc finger but can include a Plurality of zinc fingers (e.g., 2, 3, 4, 5, 6 or more fingers). Usually, the ZFPs include at least three fingers. Certain of the ZFPs include four or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

Specific examples of NT-3 and GDNF targeted ZFPs are disclosed in Tables 1 and 2. The first column in this table is an internal reference name (number) for a ZFP. "F" refers to the finger and the number following "F" refers which zinc finger (e.g., "F1" refers to finger 1).

TABLE 1

| NT-3 targeted zinc finger proteins | | | | | | |
|---|---|---|---|---|---|---|
| SBS # | Design | | | | | |
| | F6 | F5 | F4 | F3 | F2 | F1 |
| 11971 | QSGHLSR (SEQ ID NO: 3) | DRSDLSR (SEQ ID NO: 4) | DSSARKK (SEQ ID NO: 5) | RSDHLST (SEQ ID NO: 6) | RSDDRKT (SEQ ID NO: 7) | QSSHLTR (SEQ ID NO: 8) |
| 22004 | QSGHLSR (SEQ ID NO: 3) | DRSDLSR (SEQ ID NO: 4) | DSSARKK (SEQ ID NO: 5) | RSDHLST (SEQ ID NO: 6) | RPDDRNQ (SEQ ID NO: 9) | QSSHLTR (SEQ ID NO: 8) |
| 22005 | QSGHLSR (SEQ ID NO: 3) | DRSDLSR (SEQ ID NO: 4) | DSSARKK (SEQ ID NO: 5) | RSDHLST (SEQ ID NO: 6) | RKDCRTQ (SEQ ID NO: 10) | QSSHLTR (SEQ ID NO: 8) |
| 22017 | QSGHLSR (SEQ ID NO: 3) | DRSDLSR (SEQ ID NO: 4) | DSSARKK (SEQ ID NO: 5) | RSDHLST (SEQ ID NO: 6) | RHDVLAS (SEQ ID NO: 11) | QSSHLTR (SEQ ID NO: 8) |
| 22020 | QSGHLSR (SEQ ID NO: 3) | DRSDLSR (SEQ ID NO: 4) | DSSARKK (SEQ ID NO: 5) | RSDHLST (SEQ ID NO: 6) | RQDVRLA (SEQ ID NO: 12) | QSSHLTR (SEQ ID NO: 8) |
| 22055 | QSGHLSR (SEQ ID NO: 3) | QPSMLRR (SEQ ID NO: 13) | DSSARKK (SEQ ID NO: 5) | RSDHLST (SEQ ID NO: 6) | RSDDRKT (SEQ ID NO: 7) | QSSHLTR (SEQ ID NO: 8) |
| 22060 | QSGHLSR (SEQ ID NO: 3) | TAHERTR (SEQ ID NO: 14) | DSSARKK (SEQ ID NO: 5) | RSDHLST (SEQ ID NO: 6) | RSDDRKT (SEQ ID NO: 7) | QSSHLTR (SEQ ID NO: 8) |
| 22070 | QSGHLSR (SEQ ID NO: 3) | RRPDLTR (SEQ ID NO: 15) | DSSARKK (SEQ ID NO: 5) | RSDHLST (SEQ ID NO: 6) | RSDDRKT (SEQ ID NO: 7) | QSSHLTR (SEQ ID NO: 8) |
| 22091 | QSGHLSR (SEQ ID NO: 3) | DRSDLSR (SEQ ID NO: 4) | DGNTRRR (SEQ ID NO: 16) | RSSHLST (SEQ ID NO: 85) | RSDDRKT (SEQ ID NO: 7) | QSSHLTR (SEQ ID NO: 8) |

TABLE 1-continued

NT-3 targeted zinc finger proteins

| SBS # | Design | | | | | |
|---|---|---|---|---|---|---|
| | F6 | F5 | F4 | F3 | F2 | F1 |
| 22095 | QSGHLSR (SEQ ID NO: 3) | DRSDLSR (SEQ ID NO: 4) | DVSGRRA (SEQ ID NO: 17) | RSSHLST (SEQ ID NO: 85) | RSDDRKT (SEQ ID NO: 7) | QSSHLTR (SEQ ID NO: 8) |
| 22101 | QSGHLSR (SEQ ID NO: 3) | DRSDLSR (SEQ ID NO: 4) | DPNTLRR (SEQ ID NO: 18) | RSSHLST (SEQ ID NO: 85) | RSDDRKT (SEQ ID NO: 7) | QSSHLTR (SEQ ID NO: 8) |
| 22035 | QSGHLSR (SEQ ID NO: 3) | DRSDLSR (SEQ ID NO: 4) | WPQSRQR (SEQ ID NO: 19) | RSDHLSS (SEQ ID NO: 86) | RSDDRKT (SEQ ID NO: 7) | QSSHLTR (SEQ ID NO: 8) |

The target site for all the NT-3 proteins is GGAGC-CATCTGGCCGGGT (SEQ ID NO:20). This sequence is found on the plus strand of human chromosome 12 starting at 5395482 and ending at 5394399 (see, *Homo sapiens* Genome (build 35.1), NCBI). This sequence is also found on the minus strand of rat chromosome 4, starting at 1560986 and ending at 15609069 (see, *Rattus norvegicus* Genome (RGCS v3.4), NCBI).

Table 2 shows specific examples of GDNF targeted ZFPs.

TABLE 2

GDNF targeted zinc finger proteins

| ZFP name | F1 | F2 | F3 | F4 | F5 | F6 |
|---|---|---|---|---|---|---|
| 14172 | QSGHLAR (SEQ ID NO: 21) | RSDDRKT (SEQ ID NO: 7) | DNPNLNR (SEQ ID NO: 22) | RSDDLSR (SEQ ID NO: 23) | DRSHLSR (SEQ ID NO: 24) | RSDHLSR (SEQ ID NO: 25) |
| 16655 | QSGHLAR (SEQ ID NO: 21) | RSDDRKT (SEQ ID NO: 7) | RYPNLIR (SEQ ID NO: 26) | RSDDLSR (SEQ ID NO: 23) | DRSHLSR (SEQ ID NO: 24) | RSDHLSR (SEQ ID NO: 25) |
| 15961 | QSGNLAR (SEQ ID NO: 27) | TSGNLTR (SEQ ID NO: 28) | RSDHLSE (SEQ ID NO: 29) | QNHHRIN (SEQ ID NO: 30) | RSADLTR (SEQ ID NO: 31) | QSSDLRR (SEQ ID NO: 32) |
| 17248 | RSDNLSV (SEQ ID NO: 33) | RNASRIT (SEQ ID NO: 34) | QSGSLTR (SEQ ID NO: 35) | RSDNLRE (SEQ ID NO: 36) | RSDHLST (SEQ ID NO: 6) | QNATRIN (SEQ ID NO: 37) |
| 17287 | RSDHLSQ (SEQ ID NO: 38) | RSAVRKN (SEQ ID NO: 39) | RSDHLST (SEQ ID NO: 6) | DRSHLAR (SEQ ID NO: 40) | DRSARTR (SEQ ID NO: 41) | QSGNLAR (SEQ ID NO: 27) |
| 17276 | DRNQLIN (SEQ ID NO: 42) | RSADLSR (SEQ ID NO: 43) | QSSDLSR (SEQ ID NO: 44) | DRSNLTR (SEQ ID NO: 45) | RSDHLSA (SEQ ID NO: 46) | DRSDLSR (SEQ ID NO: 4) |
| 22639 | RSANLSV (SEQ ID NO: 47) | RNASRIT (SEQ ID NO: 34) | YQGVLTR (SEQ ID NO: 48) | RSDNLRE (SEQ ID NO: 36) | RSDHLST (SEQ ID NO: 6) | QNATRIN (SEQ ID NO: 37) |
| 22644 | RSDNLSV (SEQ ID NO: 33) | TKRALNQ (SEQ ID NO: 49) | QSGSLTR (SEQ ID NO: 35) | RSDNLRE (SEQ ID NO: 36) | RSDHLST (SEQ ID NO: 6) | QNATRIN (SEQ ID NO: 37) |
| 22647 | RSDNLSV (SEQ ID NO: 33) | QQSARTL (SEQ ID NO: 50) | QSGSLTR (SEQ ID NO: 35) | RSDNLRE (SEQ ID NO: 36) | RSDHLST (SEQ ID NO: 6) | QNATRIN (SEQ ID NO: 37) |
| 22653 | RSDNLSV (SEQ ID NO: 33) | HRSTLLM (SEQ ID NO: 51) | QSGSLTR (SEQ ID NO: 35) | RSDNLRE (SEQ ID NO: 36) | RSDHLST (SEQ ID NO: 6) | QNATRIN (SEQ ID NO: 37) |
| 22655 | RADNLSV (SEQ ID NO: 52) | TTKGRTH (SEQ ID NO: 53) | QSGSLTR (SEQ ID NO: 35) | RSDNLRE (SEQ ID NO: 36) | RSDHLST (SEQ ID NO: 6) | QNATRIN (SEQ ID NO: 37) |

TABLE 2-continued

GDNF targeted zinc finger proteins

| ZFP name | F1 | F2 | F3 | F4 | F5 | F6 |
| --- | --- | --- | --- | --- | --- | --- |
| 22658 | RSDNLSV (SEQ ID NO: 33) | RRSSLRS (SEQ ID NO: 54) | QSGSLTR (SEQ ID NO: 35) | RSDNLRE (SEQ ID NO: 36) | RSDHLST (SEQ ID NO: 6) | QNATRIN (SEQ ID NO: 37) |

The sequence and location for the target sites in rat, human or rhesus monkey of these GDNF-binding proteins are disclosed in Table 3. The genomic location is indicated in reference to the following UCSC genome databases: Rat (November 2004), Human (March 2006) and Rhesus (January 2006). Nucleotides in the target site that are contacted by the ZFP recognition helices are indicated in uppercase letters; non-contacted nucleotides indicated in lowercase.

TABLE 3

GDNF target sites

| ZFP name | Species | Target sequence (5'-3') | Position in species genome |
| --- | --- | --- | --- |
| 14172 | rat | GGGGGCGCGGAACCGGGA (SEQ ID NO: 55) | chr2: 57, 398, 744-57, 398, 761 |
| 16665 | rat | GGGGGCGCGGAACCGGGA (SEQ ID NO: 55) | chr2: 57, 398, 744-57, 398, 761 |
| 15961 | human | GCTGCGAGTGGGGATGAA (SEQ ID NO: 56) | chr5: 37, 876, 478-37, 876, 495 |
| 15961 | rhesus macaque | GCTGCGAGTGGGGATGAA (SEQ ID NO: 56) | chr6: 37, 682, 578-37, 682, 595 |
| 17248 22639 22644 22647 22653 22655 22658 | human | ACATGGCAGGCAATGAAG (SEQ ID NO: 58) | Chr5: 37, 876, 648-37, 876, 665 |
| 17248 22639 22644 22647 22653 22655 22658 | rhesus macaque | ACATGGCAGGCAATGAAG (SEQ ID NO: 58) | chr6: 37, 682, 748-37, 682, 765 |
| 17287 | human | GCGGAGcGGCCGGGTGAGG (SEQ ID NO: 59) | chr5: 37, 876, 435-37, 876, 453 |
| 17287 | rhesus macaque | GCGGAGcGGCCGGGTGAGG (SEQ ID NO: 59) | chr6: 37, 682, 535-37, 682, 553 |
| 17276 | human | GCCAGGgGACGCTGCGAGT (SEQ ID NO: 60) | chr5: 37, 876, 468-37, 876, 486 |
| 17276 | rhesus macaque | GCCAGGgGACGCTGCGAGT (SEQ ID NO: 60) | chr6: 37, 682, 568-37, 682, 586 |

Fusion Proteins

Fusion proteins comprising DNA-binding proteins (e.g., ZFPs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Application Publication Nos. 20050064474; 20060188987 and 2007/0218528 for details regarding fusions of DNA-binding domains and nuclease cleavage domains, incorporated by reference in their entireties herein Suitable domains for achieving activation include the HSV VP16 activation domain (see, e.g., Hagmann et al., *J. Virol.* 71, 5952-5962 (1997)); nuclear hormone receptors (see, e.g., Torchia et al., *Curr. Opin. Cell. Biol.* 10:373-383 (1998)); the p65 subunit of nuclear factor kappa B (Bitko and Barik, *J. Virol.* 72:5610-5618 (1998) and Doyle and Hunt, *Neuroreport* 8:2937-2942 (1997)); Liu et al., *Cancer Gene Ther.* 5:3-28 (1998)), or artificial chimeric functional domains such as VP64 (Seifpal et al., *EMBO J.* 11, 4961-4968 (1992)) and Degron domain (Molinari et al., *EMBO J.* 18:6439-6447 (1999) and Salghetti et al., *Proc. Natl. Acad. Sci. USA* 97:3118-3123 (2000)). Additional exemplary activation domains include, but are not limited to, p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Applications 2002/0115215 and 2003/0082552 and in co-owned WO 02/44376.

Exemplary repression domains include, but are not limited to, KRAB, KOX, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

In certain embodiments, the target site bound by the zinc finger protein is present in an accessible region of cellular chromatin. Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and US Patent Application Publication No. 2002/0160940.

Delivery

The proteins (e.g., ZFPs), nucleotides encoding same and compositions comprising the proteins and/or polynucleotides described herein may be delivered to a target cell by any suitable means. Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Zinc finger proteins as described herein may also be delivered using vectors containing sequences encoding one or more of the zinc finger protein(s). Any vector systems may be used including, but not limited to, plasmid vectors, retroviral vectors, lentiviral vectors, adenovirus vectors, poxvirus vectors; herpes virus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more zinc finger protein-encoding sequences. Thus, when one or more ZFPs are introduced into the cell, the ZFPs may be carried on the same vector or on different vectors. When multiple vectors are used, each vector may comprise a sequence encoding one or multiple ZFPs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery, to the cell. For a review of gene therapy procedures, see Anderson, *Science* 256:808-813 (1992); Nabel and Felgner, *TIBTECH* 11:211-217 (1993); Mitani and Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer and Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered ZFPs takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AVV serotypes, including AAV1 to AAV8, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pichia* and *Schizosaccharomyces*. Progeny, variants and derivatives of these cell lines can also be used.

Kits

Also described herein are kits comprising one or more of the compositions described herein (e.g., zinc finger proteins, polynucleotides encoding zinc finger proteins, fusion proteins and/or polynucleotides encoding fusion proteins). In certain embodiments, the kits generally comprise one or more containers comprising a zinc finger protein (or polynucleotide encoding same). The kits may further comprise a suitable set of instructions, generally written instructions, relating to the use of the protein or polynucleotide for any of the methods described herein (e.g., treatment of a neuropathy).

The kits comprise any convenient, appropriate packaging. The instructions generally include information as to dosage, dosing schedule, and route of administration for the intended method of use. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

Applications

The disclosed compositions and methods can be used for any application in which modulation of NT-3 or GDNF is desired, including but not limited to, therapeutic and research applications.

Diseases and conditions in which NT-3 activating ZFP TFs can be used as therapeutic agent, or stem cells containing NT-3 activating ZFP TFs, include but are not limited to, diabetic neuropathy (DN), chemotherapy-induced neuropathy, Charcot-Marie-Tooth disease, neuropathic pain, spinal cord injury, Parkinson's disease, retinal degeneration and the like.

As noted above, a VEGF-activating ZFP-TF is currently being tested for treatment of diabetic neuropathy. NT-3 activating transcription factors (e.g., ZFP-TFs) provide an alternative to these VEGF activating ZFP-TFs as activation of NT-3 does not raise safety concerns associated with induction of angiogenesis following VEGF activation. Similarly, cancer patients receiving chemotherapy often develop neuropathy. In many cancers, activation of VEGF may promote cancer progression. Thus, NT-3 ZFPs, or stem cells containing NT-3 ZFPs, provide an alternative therapy for diabetic neuropathies and chemotherapy-induced neuropathies.

Modulation (activation) of NT-3 using ZFP-TF or stem cells containing NT-3 ZFPs as described herein can also be used to treat Charcot-Marie-Tooth (CMT) disease, a common inherited neurological disorder characterized by a slowly progressive degeneration of the muscles in the foot, lower leg, hand, and forearm, and a mild loss of sensation in the limbs, fingers, and toes. There is no cure for the disease, but a recent pilot clinical study suggested that subcutaneous injection of NT-3 could provide clinical benefit. See, Sahenk et al. (2005) *Neurology* 65:681-9. NT-3 based ZFP-TF approach may prove more effective than cDNA or recombinant protein due to its ability to drive NT-3 expression at a physiologically relevant level.

Neuropathic pain, also referred to as a chronic pain, is a complex disorder resulting from injury to the nerve, spinal cord or brain. U.S. Patent Publication No. 20060040880 describes methods of treating neuropathic pain with ZFP-TF targeted to VR1, NaV1.8, and TrkA. Recently, NT-3 has been found to significantly reduce sodium channels expression that is linked to neuropathic pain states (see, e.g., Wilson-Gerwing et al. (2008) *Exp Neurol.* 213(2): 303-14., indicating that NT-3 is involved in modulating pain. In this regard, the NT-3 activating ZFP-TFs can be used to treat neuropathic pain in subjects in need of such treatment.

Similarly, GDNF-modulating ZFP-TFs, or stem cells containing GDNF ZFP TFs, can also be used to treat Parkinson's disease, Huntington's disease, retinal degeneration and amyotrophic lateral sclerosis (ALS). GDNF is a potent trophic factor for dopaminergic neurons in substantia nigra, whose loss causes Parkinson's disease. The efficacy of GDNF in animal models of Parkinson's disease has been demonstrated with both recombinant GDNF protein and overexpression of GDNF cDNA. However, clinical trials using recombinant GDNF failed to show therapeutic benefit for patients of Parkinson's disease, which may be a result of imprecise delivery of very high doses of the recombinant protein (Lang et al., 2006, supra). Accordingly, ZFP activation of GDNF, which induces more physiological level of GDNF expression, potentially provides better therapeutic outcomes.

GDNF-targeted ZFPs, or stem cells containing GDNF-targeted ZFPs can also be used to treat Huntington disease (HD), a neurodegenerative disorder with progressive loss of GABAergic medium spiny projection neurons in the striatum. GDNF has been shown to protect striatal neurons against excitotoxic lesion, and adeno-associated virus (AAV)-mediated GDNF expression in the striatum provided neuroprotection in a rat HD model. See, Kells et al. (2004) *Mol. Ther.* 9:682-288. Thus, ZFP activation of GDNF could be used to increase the production of endogenous GDNF to prevent or delay striatal neuron loss in HD patients.

Modulation of GDNF and/or NT-3 as described herein can also be used to treat or prevent retinal degeneration. Retinal degeneration includes many different conditions caused by distinct mutations, all of which leads to loss of photoreceptor cells. Diseases associated with retinal degeneration include, but are not limited to, retinitis pigmentosa, glaucoma, age-related macular degeneration (AMD) and diabetic retinopathy. GDNF has been demonstrated to promote survival of isolated photoreceptor cells in vitro; and several studies have shown that intraocular injection of GDNF protein or increased expression of GDNF by gene transfer slows rod cell death in models of retinal degeneration (Frasson et al. (1999) *Invest Ophthalmol Vis. Sci.* 40:2724-2734; McGee et al. (2001) *Mol. Ther.* 4:622-629. Thus, ZFP activators of the GDNF can be delivered intraocularly to induce physiologically relevant level of GDNF to protect photoreceptor cells. Recent evidence suggests the possibility of stem cell transplantation into retinas for treatment of AMD (Idelson et al, (2009) *Cell Stem Cell* 5(4): 396-408). Thus, stem cells containing ZFP activators of GDNF and then transplanted into degenerating retinas may represent a viable treatment for diseases associated with this condition. Similarly, NT-3 has been shown to promote retinal ganglion differentiation and survival (De La Rossa et al, (1994) *Neuroscience* 58: 347-352). Thus, ZFP TFs targeting NT-3 may protect photoreceptor cells following intraocular injection.

Zinc finger transcription factors as described herein can also be used for the treatment of amyotrophic lateral sclerosis (ALS). ALS is a progressive neurodegenerative disease caused by loss of motor neurons. GDNF has been shown to be protective for motor neurons, and AAV-mediated GDNF overexpression demonstrated neuroprotective effects in a mouse model for ALS (Wang et al. (2002) *J. Neurosci.* 22:6920-6928). Again, ZFPs targeted to GDNF, or stem cells containing GDNF specific ZFPs, which provide physiological levels of GDNF can be used to promote the survival of motor neurons in ALS patients.

The compositions described herein can also be use for the treatment of addictive behaviors. For example, increased GDNF levels have been shown to reduce addictive behavior in animal models of alcohol and drug addiction. See, Green-Sadan et al. (2005) *Exp. Neurol.* 194:97-105. ZFP activators of GDNF as described herein can be used to induce expression of endogenous GDNF and treat alcohol and/or drug addiction.

EXAMPLES

Example 1

Design and Construction of NT-3- and GDNF-Targeted Zinc Finger Proteins Transcription Factors (ZFP-TFs)

Zinc finger proteins targeted to NT-3 or GDNF were engineered essentially as described in U.S. Pat. No. 6,534,261. Table 1 shows the recognition helices of exemplary six-fingered NT-3-targeted ZFPs. Table 2 shows the recognition helices of exemplary six-fingered GDNF-targeted ZFPs.

A fusion protein was constructed and included a nuclear localization sequence, an engineered zinc finger DNA-binding domain as described herein targeted to the NT-3 gene or the GDNF gene, a p65 transcriptional activation domain of NF-kB, and a flag epitope tag. See, FIG. 1A. FIGS. 1B and 1C show exemplary NT-3 and GDNF DNA-binding domains.

Example 2

Activation of NT-3 in Human Primary Skeletal Muscle Cells

To test the feasibility of using the NT-3 activating ZFP-TF 11971 for the treatment of diabetic neuropathy via intramuscular delivery, the following experiments were conducted.

A self-inactivating HIV-derived vector RRL as described in Dull et al. (1998) *J. Virol.* 72:8463-8471 and Zufferey et al. (1998) *J. Virol.* 72:9873-9880, containing the woodchuck hepatitis post-transcriptional regulatory element (WPRE), and a polyurine tract, was modified to carry the appropriate transgene expression cassette (NT-3-targeted ZFP-TF 11971-p65 or GFP) under the control of the CMV promoter. Lentiviral vectors were prepared by transient transfection of 293T cells with 4 plasmids essentially as described in Tiscornia et al. (2006) *Nat. Protoc.* 1:241-245, the lentiviral transfer vector for specific transgene expression (i.e. ZFP TF 11971-p65, or GFP), and 3 additional packaging constructs pMDL, pREV, pVSV-G (Invitrogen), using Lipofectamine™ 2000 (Invitrogen) per manufacturer's instructions. Transfection medium was changed to growth media after 16 hours following transfection. The virus containing media were then collected after culturing for additional 24 and 48 hours and centrifuged at 3000 rpm for 10 min. The supernatant was filtered through 0.22 µM filter and concentrated 150-fold by ultracentrifugation at 28,000 rpm for 2 hours. Viral stocks were then made in small aliquots, and stored at −70° C.

The infectious titers of the virus preparation were determined as follows. First, serial diluted GFP virus was used to infect 293T cells for 2 days, and the percentage of GFP-positive cells was quantified using flow cytometry to derive the infectious titer. The infectious titer of ZFP viruses was determined by a real-time PCR based protocol to measure the copy numbers of integrated lentiviruses from the virus infected 293T cells. Briefly, 293T cells were infected with serial diluted viral stocks (ZFPs and GFP) for 2 days. Genomic DNA was then prepared and the level of proviral DNA was determined using real-time quantitative PCR (TaqMan®) as described (Liu et al. (2001) *J. Biol. Chem.* 276: 11323-11334). The copy number of proviral DNA per cell was derived by normalization to a house-keeping gene (e.g. albumin), which was also determined by quantitative PCR, in the same sample.

The proviral DNA primer/probe set (CCAACGAAGA-CAAGATCTGC (SEQ ID NO:61), TCCTGCGTC-GAGAGAGCT (SEQ ID NO:62), FAM-CGCCCGAA-CAGGGACCTGAAAGC-BHQ1 (SEQ ID NO:63)) and albumin primer/probe set (TGAAACATACGTTCCCAAA-GAGTTT (SEQ ID NO:64), CTCTCCTTCTCAGAAAGT-GTGCATAT (SEQ ID NO:65), FAM-TGCTGAAACAT-TCACCTTCCATGCAGA-BHQ1 (SEQ ID NO:66)) were used to quantify the proviral and albumin DNA respectively. The infectious titers of ZFP viral stocks were then calculated from the copy number of proviral DNA per cell using the ratio of (infectious titer)/(# of proviral DNA per cell) for the GFP virus.

The vectors were introduced into human primary skeletal muscle cells purchased from Lonza Walkersville, Inc (Walkersville, Md.) and maintained as recommended by the manufacturer.

A. Analysis of NT-3 mRNA Expression

Human NT-3 mRNA expression was analyzed as follows. Total RNA was isolated using either the High Pure RNA Isolation Kit (Roche Diagnostics) or the RNeasy™ Kit (Qiagen, Valencia, Calif.) according to the manufacturer's recommendations. Real time quantitative RT-PCR using TaqMan® chemistry in a 96-well format on an ABI 7700 SDS machine (Perkin-Elmer) was performed as described in Liu et al. (2001) *J. Biol. Chem.* 276:11323-11334. The TaqMan® primers and probes used are listed below:

```
hNT-3
                                        (SEQ ID NO: 67)
hNT3-743F     GATAAACACTGGAACTCTCAGTGCAA (SEQ ID NO: 68)
hNT3-827R     GCCAGCCCACGAGTTTATTGT (SEQ ID NO: 69)
hNT3-776P     FAM-CAAACCTACGTCCGAGCACTGACTTCAGA-BHQ1 hNT3-1A
                                        (SEQ ID NO: 70)
hNT3-1AF,     AGCCAGGATAATGATGAGATCTTACA (SEQ ID NO: 71)
hNT3-1AR,     GGAGATAAGCGAGAAATATCACATAAAA (SEQ ID NO: 72)
hNT3-1APro,   FAM-TGAACAAGGTGATGTCCA-BHQ1 hNT3-1B
                                        (SEQ ID NO: 73)
hNT3-1BF,     TCGACGTCCCTGGAAACG (SEQ ID NO: 74)
hNT3-1BR,     ACATAAAACAAGATGGACATCACCTT (SEQ ID NO: 75)
hNT3-1BPro,   FAM-TGCCATGGTTACTTTTGCCACGATCTTACA-
              BHQ1 hGAPDH
                                        (SEQ ID NO: 76)
hGAPDH-For,   CCATGTTCGTCATGGGTGTGA (SEQ ID NO: 77)
hGAPDH-Rev,   CATGGACTGTGGTCATGAGT (SEQ ID NO: 78)
hGAPDH-Pro,   FAM-TCCTGCACCACCAACTGCTTAGCA-TAMRA
```

The transcription of NT-3 is driven by two alternative promoters, promoter A and B, resulting in two alternatively started transcripts, transcript 1A and 1B. The transcript 1B is predominately expressed in cells that express NT-3 protein.

As shown in FIG. 2A, ZFP-TF 11971 preferentially promoted the expression of the NT-3 transcript 1B in human SKMC cells.

B. NT-3 Protein Expression Analysis

Secreted NT-3 protein levels were determined in the culture media after a 48-h accumulation period (i.e. 48 hours after fresh media was applied to the cells). Aliquots (200 µl) of culture media were assayed by using NT-3 Emax® ImmunoAssay System (Promega, Madison, Wis.) following the manufacturer's instructions.

As shown in FIG. 2B, cells treated with the NT-targeted ZFP-TF 11971-p65 produced much more NT-3 protein than mock transduced cells.

These results demonstrate the engineered ZFP-TF 11971-p65 is capable of activating NT-3, at both the mRNA and protein level, in human skeletal muscle cells. Since skeletal muscle is innervated with many sensory and motor neurons, promoting NT-3 expression in skeletal muscles by ZFP-TF mediated NT-3 activation can lead to a beneficial effect on the local nervous system.

Example 3

Activation of NT-3 in Rat Primary Skeletal Muscle Cells

The ability of NT-3 targeted ZFP-TFs to modulate NT-3 expression was also analyzed in rat primary skeletal muscle cells. In particular, rat primary skeletal muscle cells were prepared as described in Hellsten et al. (1997) *J. Physiol.* 504:695-704. Briefly, the muscle tissue was dissected out from the hind limbs of 21-days-old rat embryos and digested with 0.1% (w/v) collagenase and 0.2% (w/v) trypsin in phosphate-buffered saline containing 0.1% (w/v) glucose at 37° C. for 30 min. The digested tissues were resuspended in growth media (DMEM (Invitrogen) containing 10% horse serum, and 2 mM L-glutamine). The cells were dissociated by mechanical trituration with a 10 ml pipette. After centrifugation at 1000 rpm for 5 min, the cell pellet was resuspended in growth media. The cell suspension was filtered through a 100 µM nylon mesh and incubated in culture flasks for 45 min. The nonattached myoblasts were collected and maintained in 0.1% (w/v) gelatin coated plates.

Rat skeletal muscle cells were infected with lentiviral vectors encoding either 11971-p65 or GFP at a multiplicity of infection of 10~50 for 2 days. The cells and the culture media were then collected for NT-3 mRNA expression and NT-3 protein analysis, respectively. NT-3 protein levels were also analyzed as described in Example 2. For TaqMan® analysis of rat NT-3 mRNA expression levels the following primers:

```
                                       (SEQ ID NO: 79)
rNT3 778F    5'-TGTGACAGTGAGAGCCTGTGG (SEQ ID NO: 80)
rNT3 846R    5'-TGTAACCTGGTGTCCCCGAA (SEQ ID NO: 81)
rNT3 800P    5'-FAM-TGACCGACAAGTCCTCAGCCATTGAC-BHQ1

(SEQ ID NO: 82)
rGAPDH-For,  CCCATGTTTGTGATGGGTGTG (SEQ ID NO: 83)
rGAPDH-Rev,  ATCCTGCACCACCAACTGCTTAGC (SEQ ID NO: 84)
rGAPDH-Pro,  FAM-ATCCTGCACCACCAACTGCTTAGC-TAMRA
```

Figure 3:
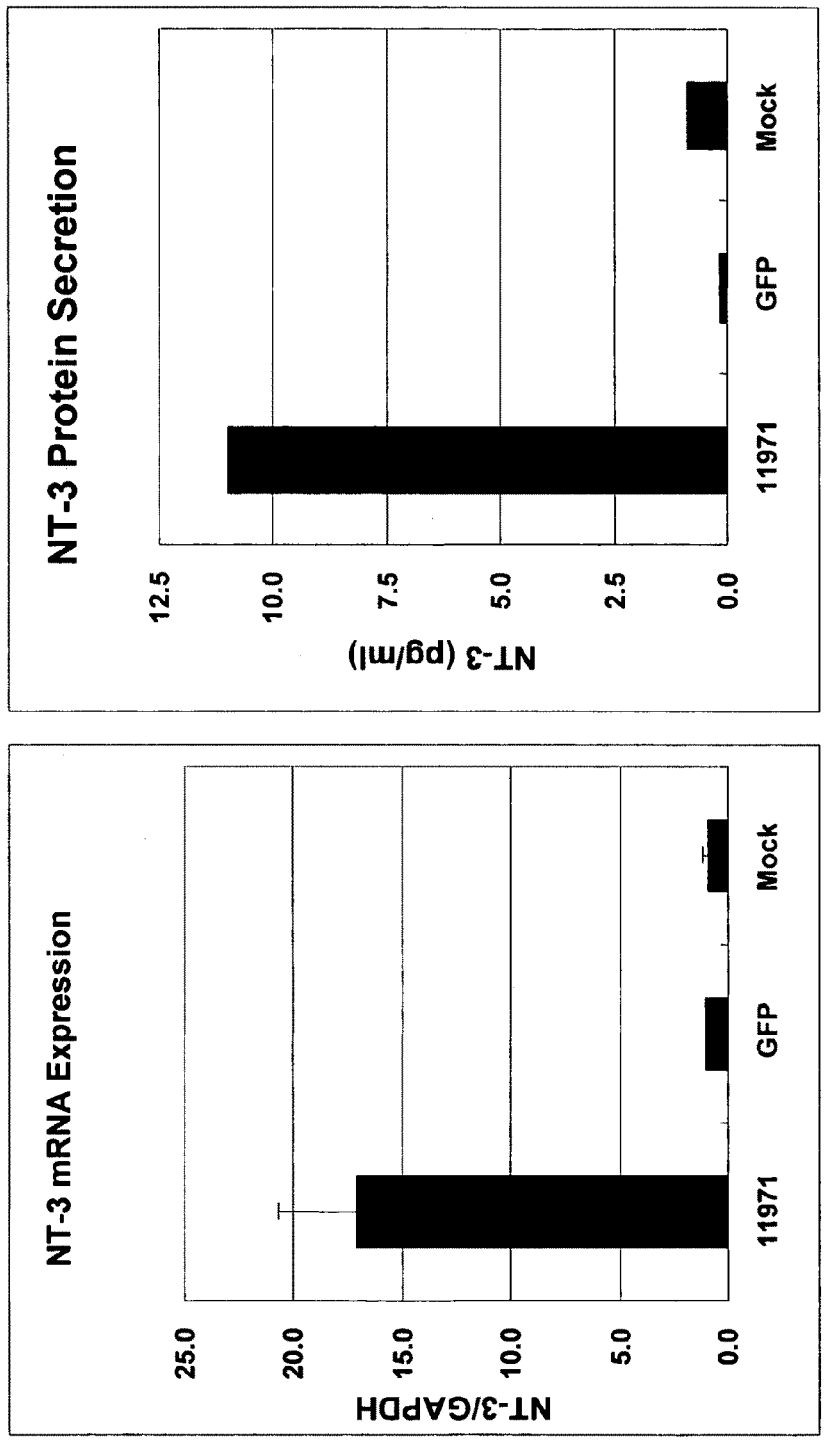
FIG. 3, panels A and B, are graphs depicting NT-3 expression in rat SKMC cells.

As shown in FIGS. 3A and 3B, transduction of lentiviral vector encoding the NT-3 targeted ZFP-TF resulted in a robust increase in both the NT-3 mRNA (FIG. 3A) and NT-3 protein levels (FIG. 3B). Thus, ZFP-TF 11971-p65 activated NT-3 gene expression in rat primary skeletal muscle cells.

Example 4

Protection of Nerve Conduction Velocity by NT-3 Targeted ZFP-TF

The efficacy of NT-3-targeted ZFP-TF against neuropathy was also tested in an established rat model of streptozotocin-induced diabetic neuropathy.

Plasmid vectors encoding the NT-3 activator ZFP-TF 11971-p65, and the VEGF activator SB509, were constructed and named here as NT3, SB509 respectively. SB509 has previously been shown to be efficacious in protection of nerve conduction velocities (NCVs) in diabetic rats. See, e.g., Price et al. (2006) *Diabetes* 55:1847-1854.

Both vectors, along with the vector control (no transgene), were formulated at a concentration of 2 mg/ml in 5% poloxamer. 188 (BASF, Washington, N.J.), 150 mmol/l NaCl, and 2 mmol/l Tris, pH 8.0.

Diabetes was induced in adult male Wistar rats (250-300 g, Charles River, UK) via intraperitoneal injection (55 mg/kg) of streptozotocin (STZ). Rats with blood glucose less than 15 mmol/l were excluded from the study. Age- and weight-matched rats were used as non-diabetic controls. STZ-diabetic rats received intramuscular injections (250 µg of either 11971, SB509, or vector only control) divided between 2 sites in their left gastrocnemius/soleus muscle at 2, 4 and 6 weeks following STZ. Age- and weight-matched rats were used as non-diabetic controls (n=8 per group).

Eight weeks following STZ treatment, rats were anesthetized with isoflurane, and electromyograms were recorded from plantar foot muscles in response to stimulation at two sites (the sciatic notch and Achilles tendon). Electromyograms were elicited via fine percutaneous electrodes connected to a Powerlab 4 stimulator (1.5-5.0, 2 ms pulses) and recorded on a Powerlab 4 with ABI Scope software. The latency difference between the two sets of M waves was calculated and related the nerve distance between the two stimulation points (measured ex vivo) in order to calculate motor nerve conduction velocity (MNCV). The H reflex latency differences were used similarly to calculate sensory nerve conduction velocity (SNCV). NCVs were measured for both the left (injected) and right (uninjected) sides. The SNCV and MNCV data is presented as group means+/−standard deviation. The critical testing was a comparison of left versus right side NCVs, which was done by paired t tests.

As shown in Table 4, STZ-treatment led to the development of diabetes, as indicated by a reduction in body weight and an increase in plasma glucose levels. None of the treatment groups resulted in a change of these indicators of diabetes.

TABLE 4

|  | Blood Glucose | Body weight (g) | |
| --- | --- | --- | --- |
| Experimental Group | (mmol/l) | starting weight | ending weight |
| control (n = 8) | 11.98 ± 1.12 | 271.6 ± 15.9 | 494.7 ± 31.4 |
| diabetic + 11971 (n = 10) | all > 27.8 | 279.5 ± 22.1 | 344 ± 25.7 |
| diabetic + empty vector (n = 9) | all > 27.8 | 267.2 ± 15.8 | 325.7 ± 24.9 |
| diabetic + SB509 (n = 9) | all > 27.8 | 272 ± 9.2 | 227.1 ± 48.3 | data are expressed as mean ± one standard deviation

As shown in FIG. 4, both NT-3 targeted ZFP-TF protected both sensory (FIG. 4A) and motor (FIG. 4B) nerve conduction velocities. Furthermore, as shown in FIG. 4, the NCVs on the treated side was significantly higher than the untreated side (n=10; SNCV, p=0.0027; MNCV, p=0.00004). This effect was similar to that of the positive control SB509, in which the NCV improvements in treated sides were also observed (n=9; SNCV, p=0.0014; MNCV, p=0.0002). No effect in NCV was observed with the empty vector controls (n=9, SNCV, p=0.59; MNCV, p=0.19). These data demonstrated the efficacy of NT-3 targeted ZFP-TFs in protecting both the sensory and motor nerve conduction velocity in the rat model of diabetic neuropathy.

Example 5

Activation of Endogenous GDNF

GDNF-targeted ZFPs as described herein were evaluated in rat, human and rhesus macaque-derived cells as follows.

A. Rat Striatal Neuronal Cultures

Day 18 embryonic Sprague/Dawley rat striatal cells were purchased from Genlantis (San Diego, Calif.) and prepared as suggested by the supplier. Briefly, the striatal tissue was treated with NeuroPapain™ for 30 minutes at 30° C. followed by trituration. Cells were then seeded onto freshly coated poly-D-lysine (Sigma) 6-well plates, at a density of 320 000 cells per well, in Neurobasal media (Invitrogen) supplemented with B27 (Invitrogen) and Glutamax™. After 3 days incubation at 37 degrees in 5% CO2, half of the medium was replaced with fresh medium and the culture was prolonged for 3-4 additional days.

The cultured rat striatal cells were infected with lentiviruses bearing either GDNF ZFP-TF 14172 or GFP at multiplicity of infection (MOI) 10-20. Forty-eight to seventy two hours-post infection, total RNA was purified from the infected cells using the High Pure RNA isolation kit from Roche and the RNA analyzed by Taqman® 7300 real-time PCR. The primers used to determine GDNF and actin levels were: Rat GDNF: Rn00569510_m1 rodent GDNF gene expression assay (Applied Biosystems) and Rat ACTB: 4352931E ACTB gene expression assay (Applied Biosystems).

In addition, the levels of secreted GDNF in cultured neurons was determined as follows. Briefly, cell supernatants were collected and subject to ELISA using the GDNF Emax Immunoassay system (Promega) with the following minor modifications: 96-well plates used were the white Fluoro-Nunc™/LumiNunc™ Plates, and the Horseradish Peroxidase revealing reagent was the supersignal west femto maximum sensitivity substrate from Pierce. In addition, block buffer was added to each sample, to a 1× final concentration.

As shown in FIGS. 5A and 5B, administration of GDNF-ZFP 14172 to rat striatal cells activated endogenous GDNF expression (FIG. 5A) and increased GDNF protein secretion into the culture (FIG. 5B).

B. Human 293LTV Cells

Human 293LTV cells were cultured in DMEM supplemented with 10% FBS. The cells were seeded at a density of 1e5 cells per well in 24-well plates, and transfected the following day with plasmid DNA encoding ZFP-TFs designated 15961, 17248, 17276 and 17287. Plasmid encoding GFP was also included as vector control. Transfection was carried out with the FuGENE® 6 reagent (Roche Applied Biosciences) using the manufacturer's protocol. Gene expression analysis was performed 48 h after transfection. In particular, total RNA was purified using the High Pure RNA isolation kit from Roche and was used for gene expression analysis using a TaqMan® 7300 real-time PCR. The primers used to determine GDNF and actin levels were: Human GDNF: Hs00181185_m1 or Hs01055329_m1 Gene expression assay (Applied Biosystems) and Human ACTB: 4352935E (Applied Biosystems).

Figure 6:
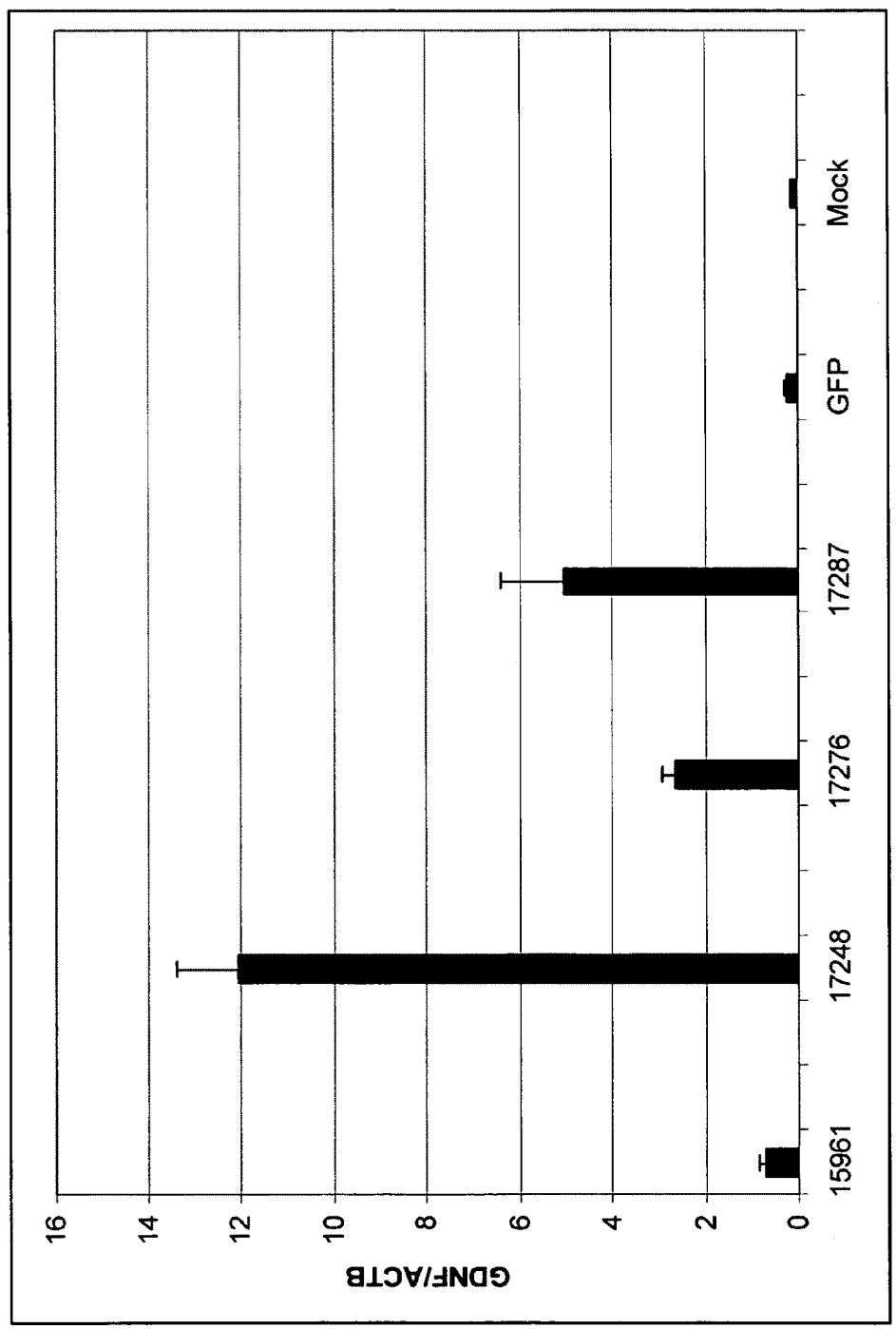
FIG. 6 is a graph showing activation of human GDNF gene in human 293LTV cells transfected with the ZFP-expressing plasmids, as compared to the cells transfected with the Green Fluorescent Protein (GFP) or an empty plasmid (Mock). GDNF and beta actin mRNA level was determined by real-time PCR and the relative GDNF level was expressed as a ratio between GDNF and beta actin (GDNF/ACTB).

As shown in FIG. 6, GDNF-targeted ZFPs as described herein activate human GDNF expression.

C. Rhesus Macaque RF6A Cells

Rhesus macaque RF6A cells were maintained in MEM supplemented with non-essential amino acids, sodium pyruvate and 10% FBS. Plasmid DNA encoding GDNF-ZFPs 15961 and 17248 (600 ng per 2e5 cells) was nucleofected using the 96-well shuttle from Amaxa using the SF solution and the EH100 program. Gene expression analysis was performed 48 h after transfection as follows. Total RNA was purified with the High Pure RNA isolation kit from Roche and was used for gene expression analysis using a TaqMan® 7300 real-time PCR. The primer/probe sets used to determine GDNF and 18S levels were:

| | |
|---|---|
| h-rh-GDNF RT-Forward:<br>CAAATGGCAGTGCTTCCTAGAAG | (SEQ ID NO: 87) |
| h-rh-GDNF RT-Reverse:<br>AGTTAAGACACAACCCCGGTTTT | (SEQ ID NO: 88) |
| h-rh-GDNF RT-Probe:<br>TGCAGCTGCCAACCCAGAGAATTCC | (SEQ ID NO: 89) |
| 18s RT-Forward:<br>TTCCGATAACGAACGAGACTCT | (SEQ ID NO: 90) |
| 18s RT-Reverse:<br>TGGCTGAACGCCACTTGTC | (SEQ ID NO: 91) |
| 18s RT-Probe:<br>TAACTAGTTACGCGACCCCCGAG | (SEQ ID NO: 92) |

Figure 7:
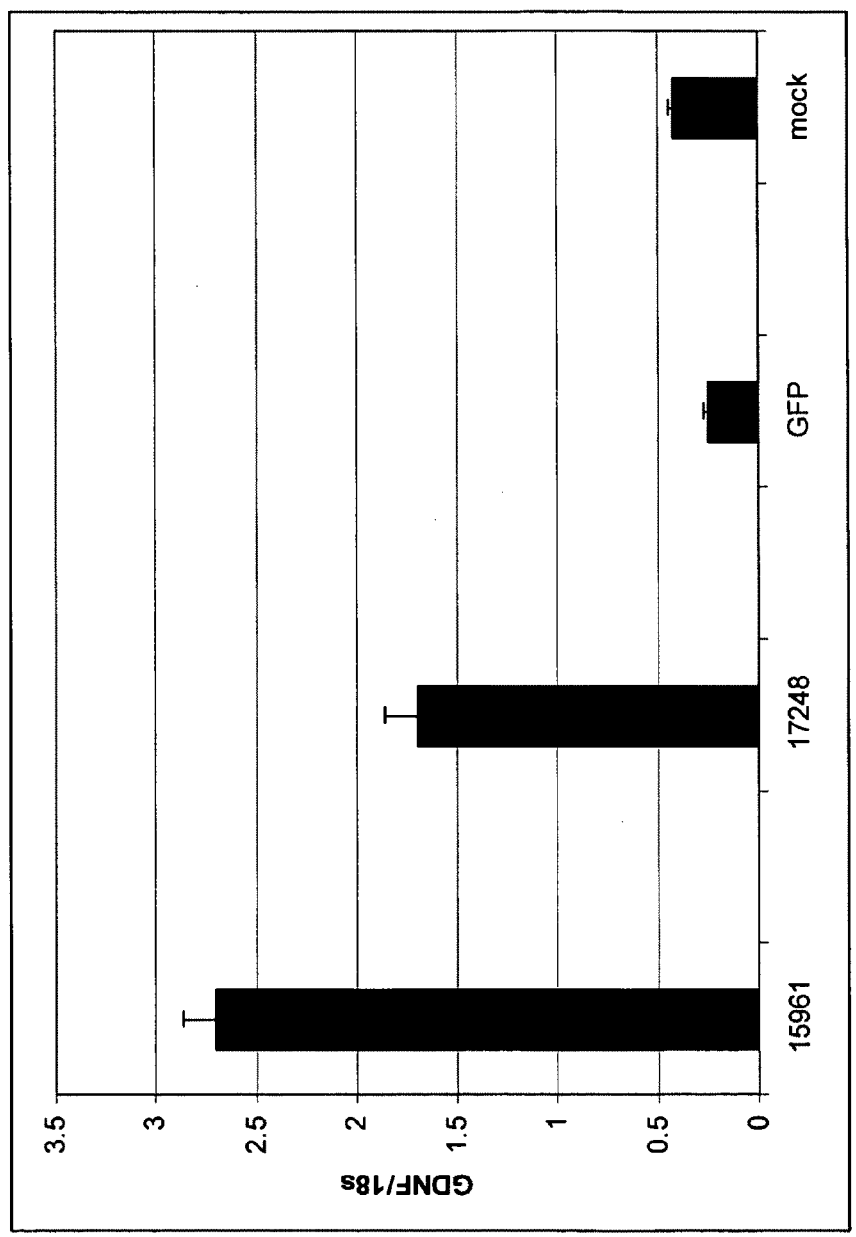
FIG. 7 is a graph showing activation of rhesus monkey GDNF gene in rhesus RF6A cells transfected with the ZFP-expressing vectors, as compared to cells transfected with the Green Fluorescent Protein (GFP) vector or mock transfected cells. GDNF mRNA levels relative to 18S are shown.

As shown in FIG. 7, GDNF-targeted ZFPs as described herein activate rhesus macaque GDNF expression.

Example 6

In vivo Analysis of GDNF-ZFPs

Rat GDNF protein levels and behavior data in the 6-hydroxydopamine (6-OHDA) model were assessed as follows. AAV vectors (GFP or GDNF-ZFP TFs) were infused bilaterally into the striatum (10 µL per striata) of adult rats (n=6 per group) using convection-enhanced delivery (CED) to maximize vector distribution within the striatum. Four weeks after vector delivery 10 µg of 6-OHDA, suspended in 20 µL sterile saline with 0.2% ascorbate, was infused into the right striata by CED. Rats were euthanized three weeks after 6-OHDA infusions.

Functional testing was undertaken after 6-OHDA infusion using three different behavioral assessments: forelimb akinesia, sensorimotor neglect, and rotational behavior.

A. Forelimb Akinesia

Forelimb akinesia was assessed using a standard "cylinder" test, essentially as described in Schallert et al. (2000) Neuropharmacology 39:777. Briefly, rats were individually placed in a vertical cylinder and placement of their left and right forepaws on the walls of the cylinder are counted as they explored the novel environment. The first 20 forepaw placements were assessed 8 and 14 days after 6-OHDA.

Figure 8:
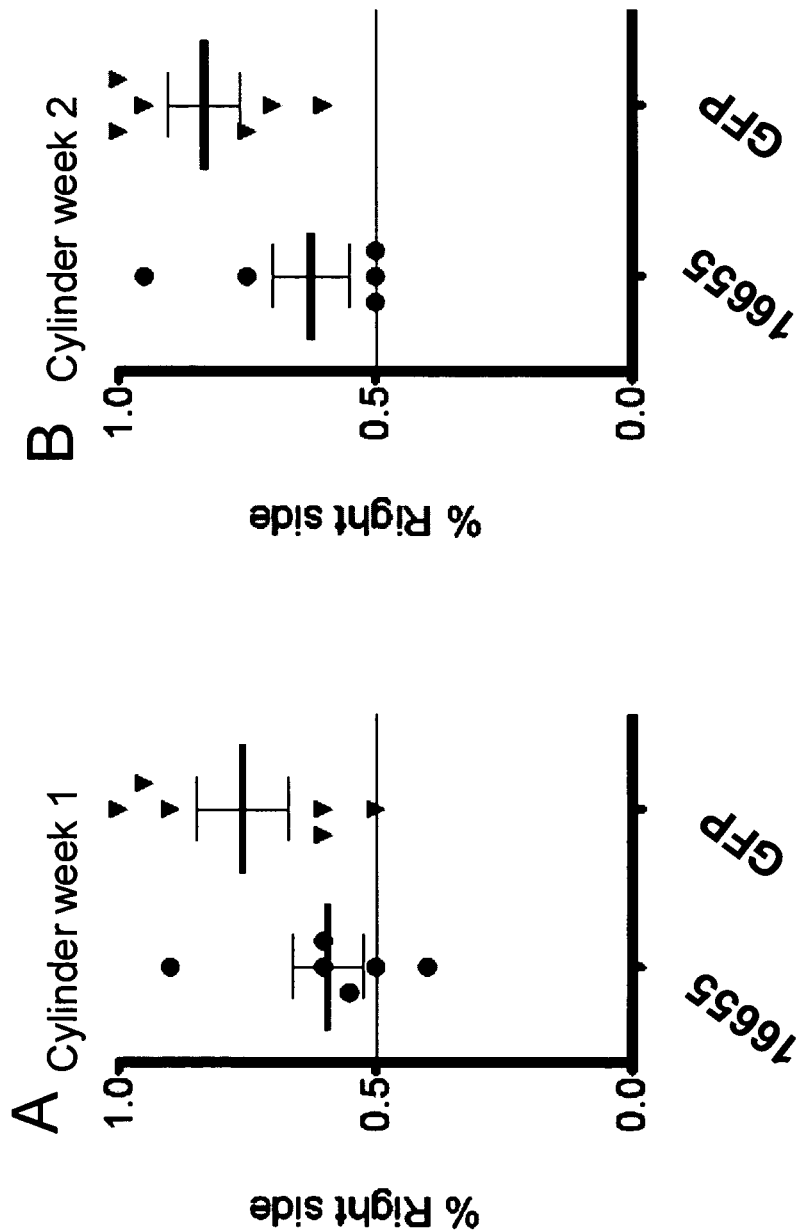
FIG. 8, panels A and B, are graphs showing forelimb akinesia in 6-OHDA lesioned rats infused with either AAV GFP vectors (control) or AAV GDNF-ZFP-TF 16655 (GDNF activating).

As shown in FIGS. 8A and 8B, at 8 days (FIG. 8A) and 14 days (FIG. 8B), after 6-OHDA administration AAV-GFPtreated rats displayed a right forelimb bias while AAV-16655 treated rats were less biased. At day 14, the AAV-16655 treated rats (62±8% right forepaw) were significantly less biased than the AAV2-GFP treated rats (83±7%; Mann-Whitney P<0.05).

B. Sensorimotor Neglect

Sensorimotor neglect was assessed using the "corridor task" as described in Fitzsimmons et al. (2006) *Behav Brain Res* 169:352, in which retrieval of food from left or right side of a corridor was monitored. The first 20 food retrievals were recorded 9 days post 6-OHDA administration.

Figure 9:
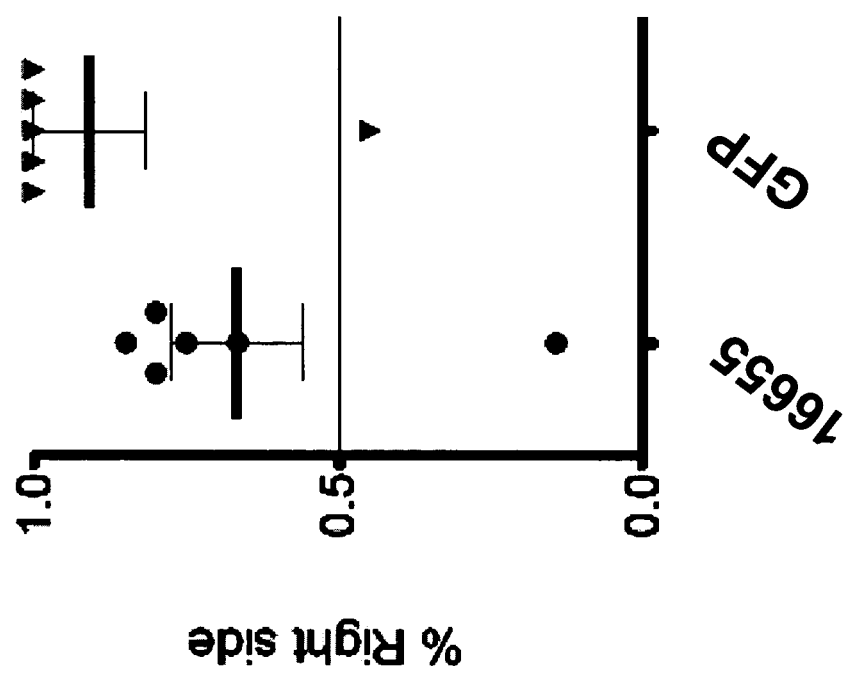
FIG. 9 is a graph depicting results of sensorimotor neglect using a "corridor task" behavior test in 6-OHDA lesioned rats infused with either AAV GFP vectors (control) or AAV GDNF-ZFP-TF 16655 (GDNF activating).

As shown in FIG. 9, following 6-OHDA administration, most rats showed a left side (contralateral) sensorimotor neglect. Assessment 9 days after 6-OHDA administration showed that GFP control rats were biased to the right with 5 of the 6 rats taking food solely from the right side of the corridor. AAV-16655 vector treated rats were less biased selecting food from the right side of the corridor only 66±11% of the time; a significant effect compared to AAV2-GFP controls (Mann-Whitney P<0.05).

C. Rotational Behavior

Amphetamine induces the release of dopamine from the terminals of dopaminergic neurons. Unilateral lesioning of the dopaminergic neurons causes a large imbalance in dopamine that causes the rats to rotate towards the lesioned side when given amphetamine. Accordingly, amphetamine-induced rotational behavior was assessed as described in Oiwa et al. (2003) *Neurosurg* 98:136 using an automated rotameter to count number of rotations induced following intraperitoneal administration of 5 mg/kg D-amphetamine. Rats were assessed 15 days post 6-OHDA for 1 hour after amphetamine injection.

Figure 10:
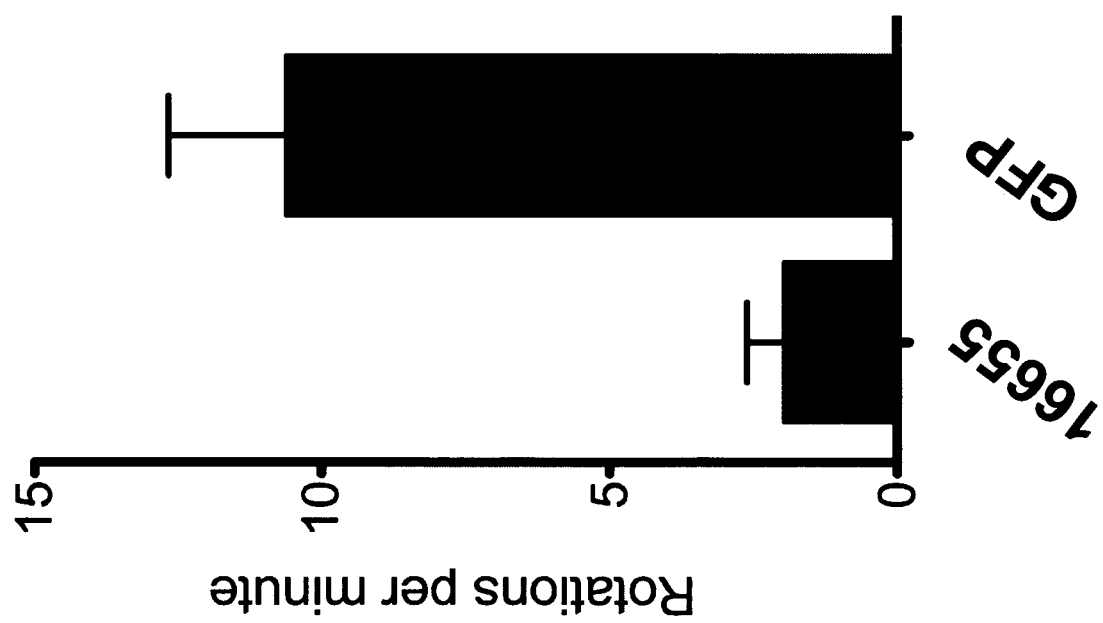
FIG. 10 is a graph depicting amphetamine-induced rotational behavior in 6-OHDA lesioned rats infused with either AAV GFP vectors (control) or AAV GDNF-ZFP-TF 16655 (GDNF activating).

Treatment with AAV2-16655 resulted in a significant reduction in the extent of rotational behavior 2 weeks after 6-OHDA administration compared to the AAV2-GFP treated rats. AAV-16655 gave a great level of protection with these rats showing only 2.0±0.6 rotations per minute compared to 10.6±2.0 for control AAV2-GFP rats. See, FIG. 10.

D. GDNF Expression

Concentrations of GDNF protein in rats receiving GDNF ZFP-TFs and control rats were also determined with a commercially available kit (Promega Corporation, Madison, Wis.). Control AAV1 and AAV2 GFP vectors or AAV1 and AAV2 vectors of 14172 and GFP were infused by convection enhanced delivery (CED) and the complete striatum dissected 3 weeks after infusion. In addition, the complete striatum was also dissected from each hemisphere of the behaviorally tested rats infused with AAV-16655 and treated with 6-OHDA. Striatal tissue was snap frozen in liquid nitrogen and homogenized with a model 100 Fisher Science Dismembrator in 300 uL of lysis buffer (Tropix, Applied Biosciences, Foster City, Calif.) supplemented with protease inhibitors (Mini Complete, Roche, Palo Alto, Calif.) and then centrifuged for 15 min at 13,000 rpm at 4° C. Standard, kit control or samples were added in duplicate to wells coated with antibody specific for GDNF.

After a 5 hour incubation, wells were washed thoroughly, and enzyme-linked polyclonal antibodies against GDNF added to each well that were allowed to incubate overnight. Next, plates were washed and incubated with peroxidase-labeled secondary antibody for 2 hours. Then, substrate solution (Supersignal; Pierce, Milwaukee, Wis.) was added to each well and plates were read after a 5-min incubation. Chemiluminescence was measured on a Flx800 microplate reader (Biotek, Winooski, Vt.) expressed as relative light units (RLU). Concentration of GDNF in tissue extracts (pg/mL) was then calculated by reference to a standard curve.

Figure 11:
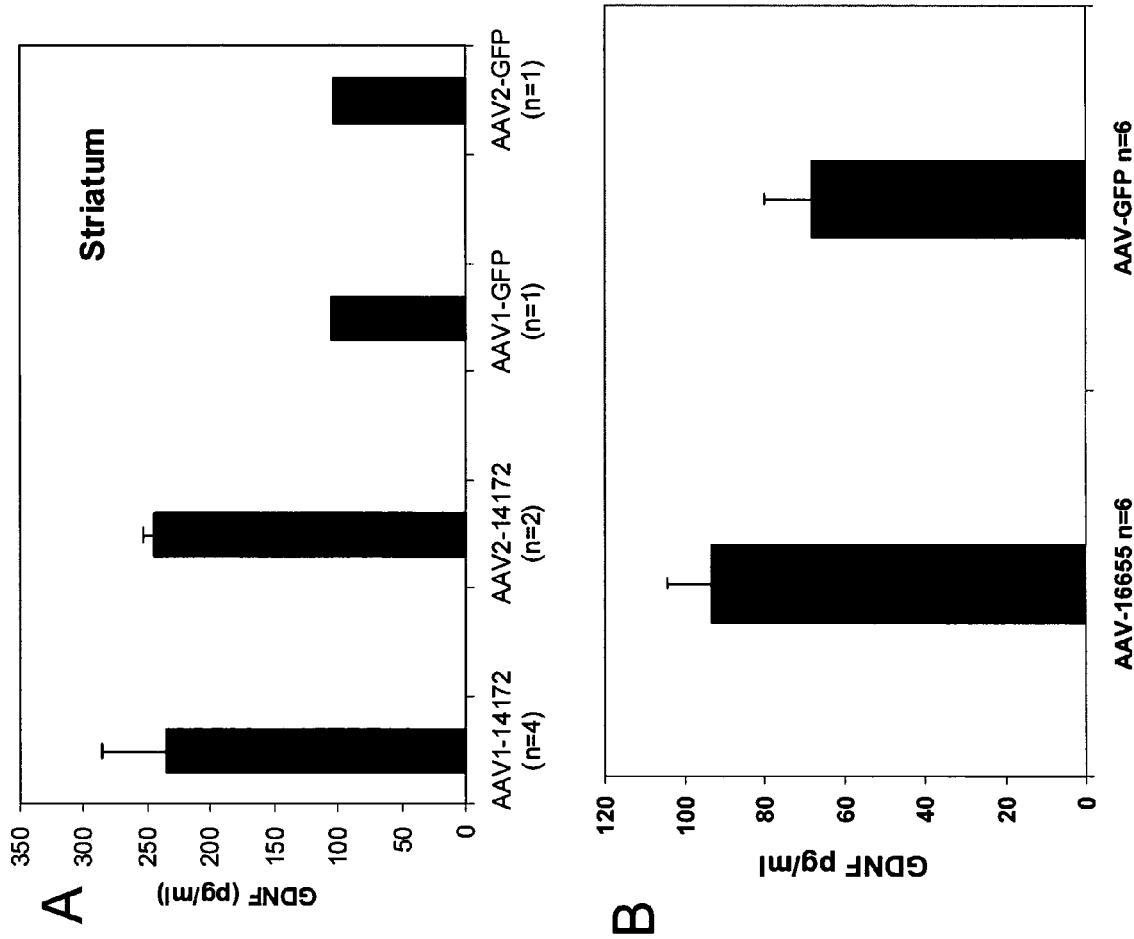
FIG. 11, panels A and B, are graphs depicting GDNF protein expression as measured by ELISA in rat striatal tissue from rats infused with AAV1 or AAV2 GDNF-ZFP-TFs 14172 or 16655 or control vectors.

As shown in FIGS. 11A and 11B, all ZFP-TFs treated rats had more GDNF protein in striatal tissue than control rats.

Example 7

Improved NT-3 Protein Activation by Alternative Activation Domains

HEK 293T cells were transiently transfected with 0.5 ug of plasmids containing one p65 domain linked to the 11971 ZFP (11971-p65) or containing two p65 domains linked either to the 11971 ZFP (11971-2x p65) or to the 23570 ZFP (23570-2x p65) by Lipofectamine 2000 (Invitrogen) as per manufacturer's instructions. Secreted NT-3 protein levels were determined in the culture media after 48 hours. Aliquots (200 ul) of culture media were assayed by using NT-3 Emax ImmunoAssay System (Promega, Madison, Wis.) following the manufacturer's instructions. Controls included transfection with a GFP expression plasmid and an empty vector (pcDNA).

Figure 12:
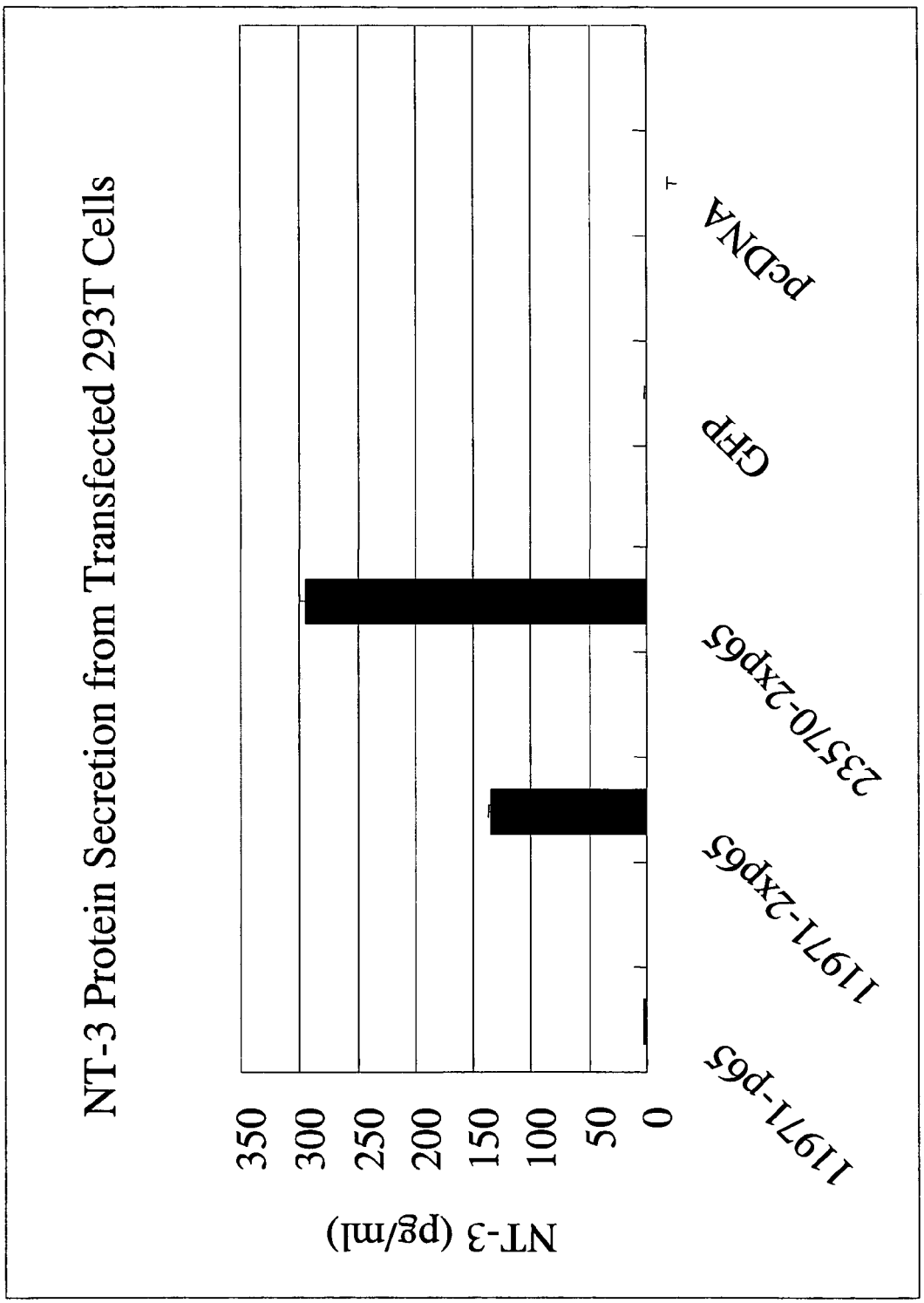
FIG. 12 is a graph depicting NT-3 protein secretion in 293T cells transfected with different ZFP TF constructs. Constructs contained either one (11971-p65) or two (11971-2xp65 and 23570-2xp65) p65 activation domains. Controls were either a GFP encoding plasmid (GFP) or empty vector (pcDNA).

As shown in FIG. 12, cells treated with ZFP candidates containing two copies of p65 activation domain (11971-2x p65 or 23570-2xp65) produced at least 10-fold more of NT-3 protein than cells transfected with 11971-p65. Thus 2 copies of p65 activation domain acts more efficiently than single p65 domain for driving NT-3 activation. The result confirms robust NT-3 activation by 11971 or 23570 ZFPs.

Example 8

Activation of Human GDNF in Human 293 LTV Cells

Figure 13:
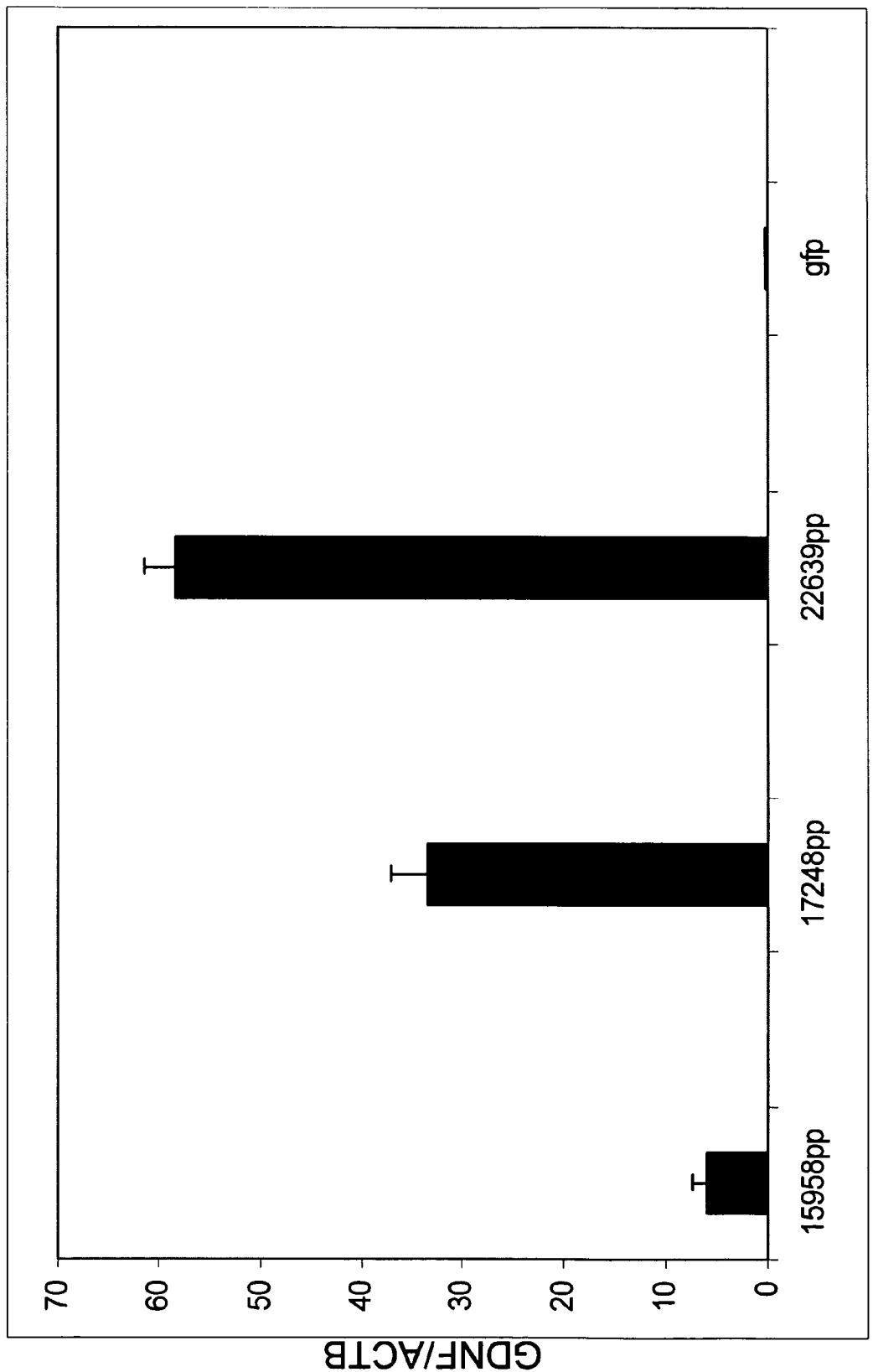
FIG. 13 is a graph depicting activation of human GDNF gene in human 293LTV cells transfected with the ZFP-expressing plasmids as compared to the cells transfected with the Green Fluorescent Protein (GFP) expressing plasmid. GDNF and beta actin mRNA levels were determined by real-time PCR and the relative GDNF level was expressed as a ratio between GDNF and beta actin (GDNF/ACTB).

FIG. 13 is a graph showing activation of human GDNF gene in human 293LTV cells transfected with the ZFP-expressing plasmids using Fugene® 6 (Roche), as compared to the cells transfected with the Green Fluorescent Protein (GFP) expressing plasmid. GDNF and beta actin mRNA levels were determined by real-time PCR and the relative GDNF level was expressed as a ratio between GDNF and beta actin (GDNF/ACTB) as described above in Example 5. This result confirms GDNF activation by the GDNF-specific ZFPs.

Example 9

Activation of Rhesus Monkey GDNF Expression in Rhesus LLC-MK2 Cells

Figure 14:
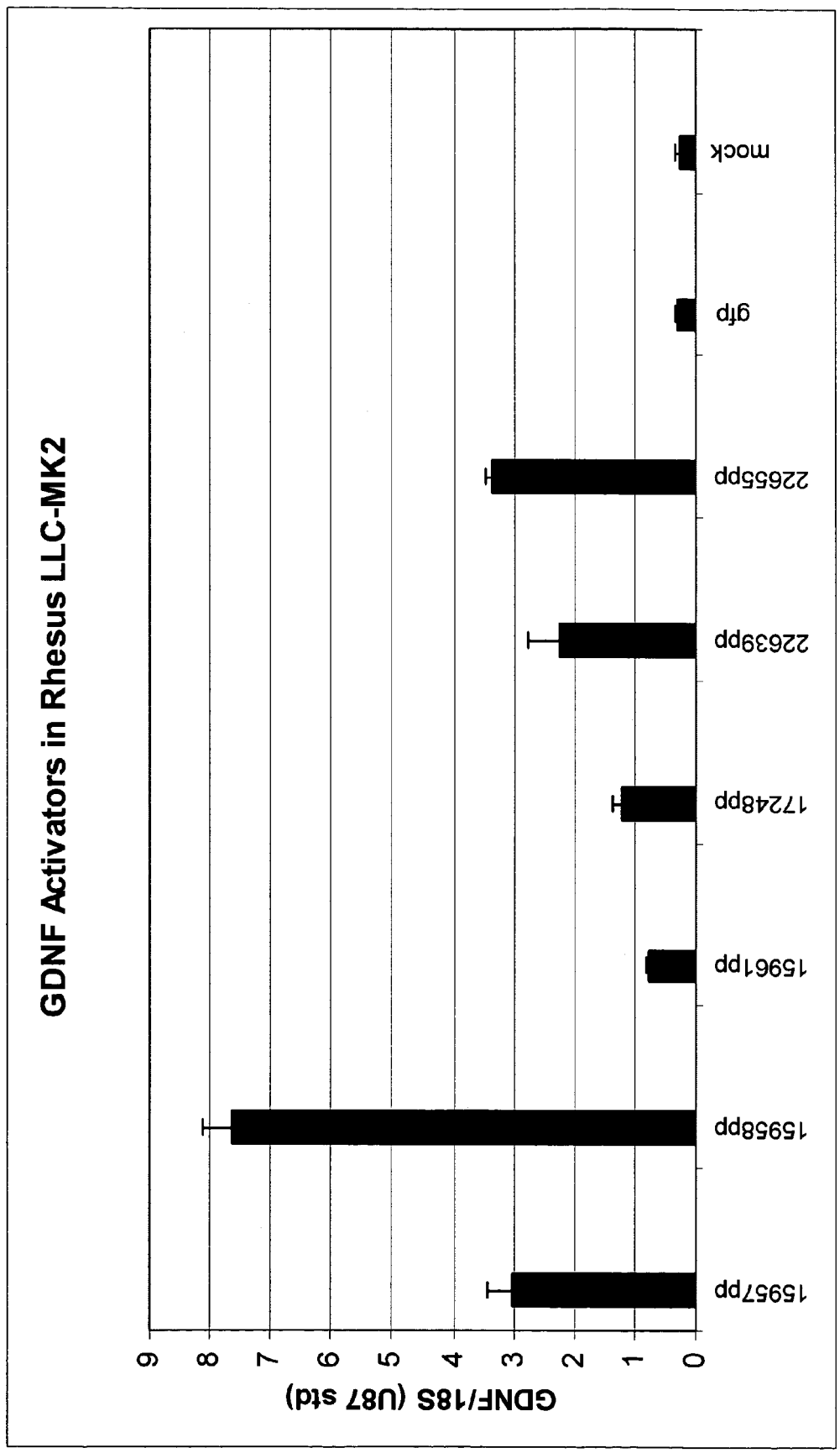
FIG. 14 is a graph showing activation of the rhesus monkey GDNF gene in rhesus LLC-MK2 cells nucleofected with the ZFP-expressing vectors, as compared to cells transfected with the Green Fluorescent Protein (GFP) vector or mock transfected cells. GDNF mRNA levels relative to 18S are shown.

LLC-MK2 cells were maintained in Opti-MEM (Invitrogen) supplemented with 10% FBS and nucleofected using Amaxa's single cuvette nucleofection technology (Lonza AG) using program A-23. Total RNA was extracted after 48 h, and real-time PCR was performed with primers describe in Example 5. FIG. 14 shows activation of rhesus monkey GDNF gene in rhesus LLC-MK2 cells nucleofected with the ZFP-expressing vectors, as compared to cells transfected with the Green Fluorescent Protein (GFP) vector or mock transfected cells. GDNF levels relative to 18S are shown. This data shows that these ZFP expression vectors are capable of inducing GDNF expression in rhesus cells.

Example 10

Stimulation of Rat GDNF in the Eye in vivo

Figure 15:
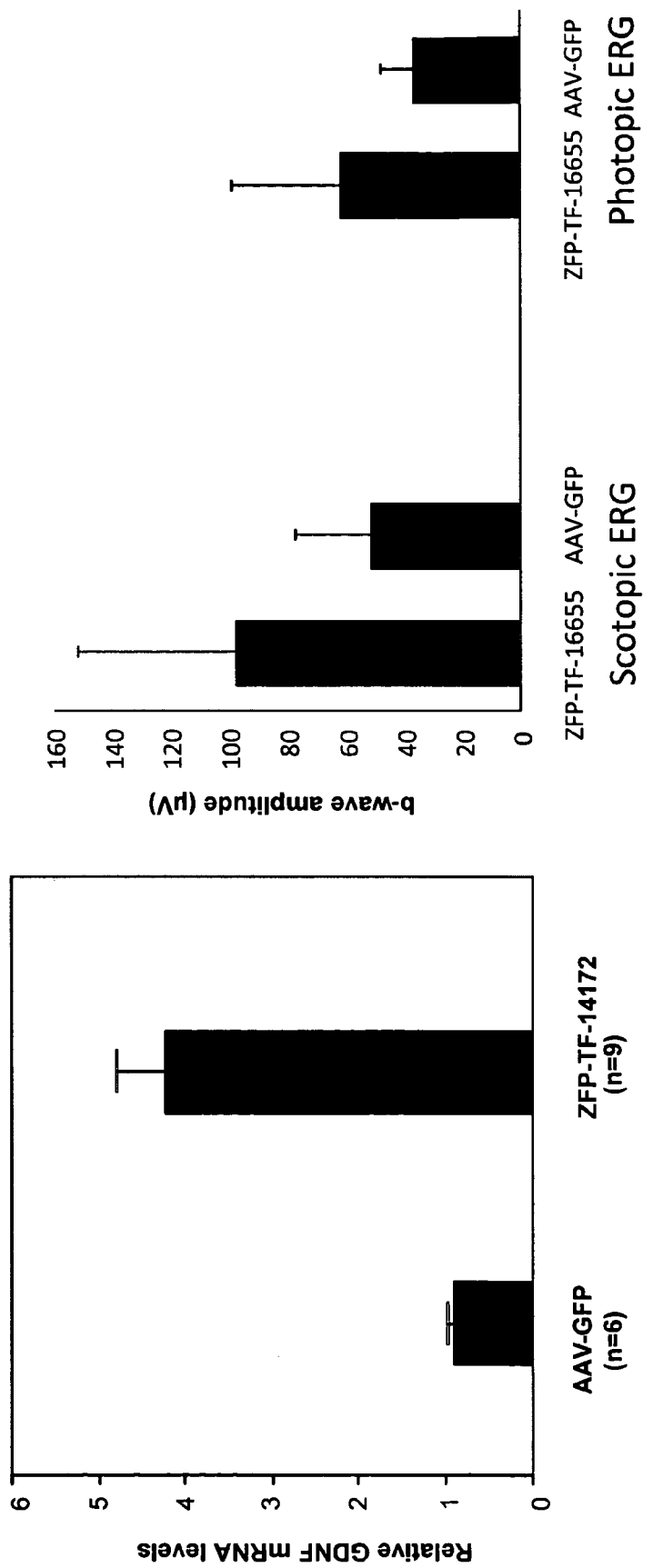
FIG. 15, panels A and B, show activity of rat specific GDNF ZFP TFs in vivo.

AAV-2 vectors encoding the rat GDNF activator (AAV ZFP TF-14172) and the GFP control (AAV-GFP) were injected into subretinal space of normal rats. Six weeks after injection, RNA was isolated from eyecups and the levels of GDNF mRNA were measured by real-time RT-PCR. A ~5-fold increase in GDNF mRNA levels was observed in eyes injected with AAV2 ZFP TF-14172 compare to those injected with AAV-GFP (see FIG. 15), demonstrating the activity of the GDNF-specific ZFPs in vivo.

Example 11

Preservation of Cone Function in RCS Rats

At postnatal day 21(P21), subretinal injections of AAV-GFP or AAV-16655 were done in RCS (Royal College of Surgeon) rats. RCS rats carry a mutation in the Mertk gene that causes autosomal recessive retinitis pigmentosa in human. At P60, electroretinograms (ERGs) were performed to evaluate the function of rod and cone photoreceptor cells. With a stimulus intensity of 4cd-s/m2, mean scotopic b-wave amplitude was 97.9±54.3 µV in eyes injected with AAV-16655 compared to 51.9±26.0 µV in eyes injected with AAV-GFP (p=0.0006), suggesting the preservation of rod function (see FIG. 15). With a stimulus intensity of 25cd-s/m2, mean photopic b-wave amplitudes were 62.5±36.9 in eyes injected with AAV-16655 compared to 37.7±10.8 µV in eyes injected with AAV-GFP (p=0.0058), suggesting the preservation of cone function.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An engineered zinc finger protein that modulates expression of NT-3 or GDNF, wherein the engineered zinc finger protein comprises six recognition helix regions ordered F1 to F6 and wherein the zinc finger protein is selected from the group consisting of a protein comprising the following amino acid sequences in the recognition helix regions:

(i)
F1: QSSHLTR (SEQ ID NO: 8);
F2: RSDDRKT (SEQ ID NO: 7);
F3: RSDHLST (SEQ ID NO: 6);
F4: DSSARKK (SEQ ID NO: 5);
F5: DRSDLSR (SEQ ID NO: 4); and
F6: QSGHLSR (SEQ ID NO: 3);

(ii)
F1: QSSHLTR (SEQ ID NO: 8);
F2: RPDDRNQ (SEQ ID NO: 9);
F3: RSDHLST (SEQ ID NO: 6);
F4: DSSARKK (SEQ ID NO: 5);
F5: DRSDLSR (SEQ ID NO: 4); and
F6: QSGHLSR (SEQ ID NO: 3);

(iii)
F1: QSSHLTR (SEQ ID NO: 8);
F2: RKDCRTQ (SEQ ID NO: 10);
F3: RSDHLST (SEQ ID NO: 6);
F4: DSSARKK (SEQ ID NO: 5);
F5: DRSDLSR (SEQ ID NO: 4); and
F6: QSGHLSR (SEQ ID NO: 3);

(iv)
F1: QSSHLTR (SEQ ID NO: 8);
F2: RHDVLAS (SEQ ID NO: 11);
F3: RSDHLST (SEQ ID NO: 6);
F4: DSSARKK (SEQ ID NO: 5);
F5: DRSDLSR (SEQ ID NO: 4); and
F6: QSGHLSR (SEQ ID NO: 3);

(v)
F1: QSSHLTR (SEQ ID NO: 8);
F2: RQDVRLA (SEQ ID NO: 12);
F3: RSDHLST (SEQ ID NO: 6);
F4: DSSARKK (SEQ ID NO: 5);
F5: DRSDLSR (SEQ ID NO: 4); and
F6: QSGHLSR (SEQ ID NO: 3);

(vi)
F1: QSSHLTR (SEQ ID NO: 8);
F2: RSDDRKT (SEQ ID NO: 7);
F3: RSDHLST (SEQ ID NO: 6);
F4: DSSARKK (SEQ ID NO: 5);
F5: QPSMLRR (SEQ ID NO: 13); and
F6: QSGHLSR (SEQ ID NO: 3);

(vii)
F1: QSSHLTR (SEQ ID NO: 8);
F2: RSDDRKT (SEQ ID NO: 7);

|       |     |         |                    |        |     |         |                     |
|-------|-----|---------|--------------------|--------|-----|---------|---------------------|
|       | F3: | RSDHLST | (SEQ ID NO: 6);    | (xiv)  | F1: | QSGHLAR | (SEQ ID NO: 21);    |
|       | F4: | DSSARKK | (SEQ ID NO: 5);    |        | F2: | RSDDRKT | (SEQ ID NO: 7);     |
|       | F5: | TAHERTR | (SEQ ID NO: 14); and |      | F3: | RYPNLIR | (SEQ ID NO: 26);    |
|       | F6: | QSGHLSR | (SEQ ID NO: 3);    |        | F4: | RSDDLSR | (SEQ ID NO: 23);    |
| (viii)| F1: | QSSHLTR | (SEQ ID NO: 8);    |        | F5: | DRSHLSR | (SEQ ID NO: 24); and|
|       | F2: | RSDDRKT | (SEQ ID NO: 7);    |        | F6: | RSDHLSR | (SEQ ID NO: 25);    |
|       | F3: | RSDHLST | (SEQ ID NO: 6);    | (xv)   | F1: | QSGNLAR | (SEQ ID NO: 27);    |
|       | F4: | DSSARKK | (SEQ ID NO: 5);    |        | F2: | TSGNLTR | (SEQ ID NO: 28);    |
|       | F5: | RRPDLTR | (SEQ ID NO: 15); and |      | F3: | RSDHLSE | (SEQ ID NO: 29);    |
|       | F6: | QSGHLSR | (SEQ ID NO: 3);    |        | F4: | QNHHRIN | (SEQ ID NO: 30):    |
| (ix)  | F1: | QSSHLTR | (SEQ ID NO: 8);    |        | F5: | RSADLTR | (SEQ ID NO: 31); and|
|       | F2: | RSDDRKT | (SEQ ID NO: 7);    |        | F6: | QSSDLRR | (SEQ ID NO: 32);    |
|       | F3: | RSSHLST | (SEQ ID NO: 85);   | (xvi)  | F1: | RSDNLSV | (SEQ ID NO: 33);    |
|       | F4: | DGNTRRR | (SEQ ID NO: 16);   |        | F2: | RNASRIT | (SEQ ID NO: 34);    |
|       | F5: | DRSDLSR | (SEQ ID NO: 4); and |       | F3: | QSGSLTR | (SEQ ID NO: 35);    |
|       | F6: | QSGHLSR | (SEQ ID NO: 3);    |        | F4: | RSDNLRE | (SEQ ID NO: 36);    |
| (x)   | F1: | QSSHLTR | (SEQ ID NO: 8);    |        | F5: | RSDHLST | (SEQ ID NO: 6); and |
|       | F2: | RSDDRKT | (SEQ ID NO: 7);    |        | F6: | QNATRIN | (SEQ ID NO: 37);    |
|       | F3: | RSSHLST | (SEQ ID NO: 85);   | (xvii) | F1: | RSDHLSQ | (SEQ ID NO: 38);    |
|       | F4: | DVSGRRA | (SEQ ID NO: 17);   |        | F2: | RSAVRKN | (SEQ ID NO: 39);    |
|       | F5: | DRSDLSR | (SEQ ID NO: 4); and |       | F3: | RSDHLST | (SEQ ID NO: 6);     |
|       | F6: | QSGHLSR | (SEQ ID NO: 3);    |        | F4: | DRSHLAR | (SEQ ID NO: 40);    |
| (xi)  | F1: | QSSHLTR | (SEQ ID NO: 8);    |        | F5: | DRSARTR | (SEQ ID NO: 41); and|
|       | F2: | RSDDRKT | (SEQ ID NO: 7);    |        | F6: | QSGNLAR | (SEQ ID NO: 27);    |
|       | F3: | RSSHLST | (SEQ ID NO: 85);   | (xviii)| F1: | DRNQLIN | (SEQ ID NO: 42);    |
|       | F4: | DPNTLRR | (SEQ ID NO: 18);   |        | F2: | RSADLSR | (SEQ ID NO: 43);    |
|       | F5: | DRSDLSR | (SEQ ID NO: 4); and |       | F3: | QSSDLSR | (SEQ ID NO: 44);    |
|       | F6: | QSGHLSR | (SEQ ID NO: 3);    |        | F4: | DRSNLTR | (SEQ ID NO: 45);    |
| (xii) | F1: | QSSHLTR | (SEQ ID NO: 8);    |        | F5: | RSDHLSA | (SEQ ID NO: 46); and|
|       | F2: | RSDDRKT | (SEQ ID NO: 7);    |        | F6: | DRSDLSR | (SEQ ID NO: 4);     |
|       | F3: | RSDHLSS | (SEQ ID NO: 86);   | (xix)  | F1: | RSANLSV | (SEQ ID NO: 47);    |
|       | F4: | WPQSRQR | (SEQ ID NO: 19);   |        | F2: | RNASRIT | (SEQ ID NO: 34);    |
|       | F5: | DRSDLSR | (SEQ ID NO: 4); and |       | F3: | YQGVLTR | (SEQ ID NO: 48);    |
|       | F6: | QSGHLSR | (SEQ ID NO: 3);    |        | F4: | RSDNLRE | (SEQ ID NO: 36);    |
| (xiii)| F1: | QSGHLAR | (SEQ ID NO: 21);   |        | F5: | RSDHLST | (SEQ ID NO: 6); and |
|       | F2: | RSDDRKT | (SEQ ID NO: 7);    |        | F6: | QNATRIN | (SEQ ID NO: 37);    |
|       | F3: | DNPNLNR | (SEQ ID NO: 22);   | (xx)   | F1: | RSDNLSV | (SEQ ID NO: 33);    |
|       | F4: | RSDDLSR | (SEQ ID NO: 23);   |        | F2: | TKRALNQ | (SEQ ID NO: 49);    |
|       | F5: | DRSHLSR | (SEQ ID NO: 24); and |      | F3: | QSGSLTR | (SEQ ID NO: 35);    |
|       | F6: | RSDHLSR | (SEQ ID NO: 25);   |        | F4: | RSDNLRE | (SEQ ID NO: 36);    |

```
            F5: RSDHLST     (SEQ ID NO: 6); and
            F6: QNATRIN     (SEQ ID NO: 37);
   (xxi)    F1: RSDNLSV     (SEQ ID NO: 33);
            F2: QQSARTL     (SEQ ID NO: 50);
            F3: QSGSLTR     (SEQ ID NO: 35);
            F4: RSDNLRE     (SEQ ID NO: 36);
            F5: RSDHLST     (SEQ ID NO: 6); and
            F6: QNATRIN     (SEQ ID NO: 37);
   (xxii)   F1: RSDNLSV     (SEQ ID NO: 33);
            F2: HRSTLLM     (SEQ ID NO: 51);
            F3: QSGSLTR     (SEQ ID NO: 35);
            F4: RSDNLRE     (SEQ ID NO: 36);
            F5: RSDHLST     (SEQ ID NO: 6); and
            F6: QNATRIN     (SEQ ID NO: 37);
   (xxiii)  F1: RADNLSV     (SEQ ID NO: 52);
            F2: TTKGRTH     (SEQ ID NO: 53);
            F3: QSGSLTR     (SEQ ID NO: 35);
            F4: RSDNLRE     (SEQ ID NO: 36);
            F5: RSDHLST     (SEQ ID NO: 6); and
            F6: QNATRIN     (SEQ ID NO: 37); and
   (xxiv)   F1: RSDNLSV     (SEQ ID NO: 33);
            F2: RRSSLRS     (SEQ ID NO: 54);
            F3: QSGSLTR     (SEQ ID NO: 35);
            F4: RSDNLRE     (SEQ ID NO: 36);
            F5: RSDHLST     (SEQ ID NO: 6); and
            F6: QNATRIN     (SEQ ID NO: 37).
```

2. A fusion protein comprising a zinc finger protein according to claim 1 and a functional domain.

3. The fusion protein of claim 2, wherein the functional domain is a transcriptional regulatory domain.

4. The fusion protein of claim 3, wherein the transcriptional regulatory domain is an activation domain.

5. The fusion protein of claim 3, wherein the transcriptional regulatory domain is a repression domain.

6. A polynucleotide encoding a zinc finger protein according to claim 1.

7. A pharmaceutical composition comprising a zinc finger protein according to claim 1.

8. A pharmaceutical composition comprising a polynucleotide according to claim 6.

9. An isolated cell comprising a zinc finger protein according to claim 1.

10. The isolated cell of claim 9, wherein the cell is a stem cell.

11. An isolated cell comprising a polynucleotide according to claim 6.

12. The isolated cell of claim 11, wherein the cell is a stem cell.

13. A method of activating NT-3 or GDNF in a cell, the method comprising introducing the zinc finger protein of claim 1 in a cell in vitro.

14. The method of claim 13, wherein the zinc finger protein is administered as a polynucleotide encoding the zinc finger protein.

15. The method of claim 14, wherein the polynucleotide is carried by a viral vector.

16. The method of claim 14, wherein the polynucleotide is carried by a non-viral vector.

\* \* \* \* \*